(12) United States Patent
Nadal et al.

(10) Patent No.: US 10,465,030 B2
(45) Date of Patent: Nov. 5, 2019

(54) NANOPARTICLES COMPLEXED WITH FUNCTIONALIZABLE ENHANCED AFFINITY LIGANDS AND USE THEREOF

(71) Applicant: NEXDOT, Paris (FR)

(72) Inventors: Brice Nadal, Paris (FR); Chloe Grazon, Paris (FR); Stephanie Deville, Paris (FR)

(73) Assignee: NEXDOT, Paris (FR)

( * ) Notice: Subject to any disclaimer, the term of this patent is extended or adjusted under 35 U.S.C. 154(b) by 0 days.

(21) Appl. No.: 15/101,516

(22) PCT Filed: Dec. 4, 2014

(86) PCT No.: PCT/EP2014/076655
§ 371 (c)(1),
(2) Date: Jun. 3, 2016

(87) PCT Pub. No.: WO2015/082656
PCT Pub. Date: Jun. 11, 2015

(65) Prior Publication Data
US 2016/0304648 A1    Oct. 20, 2016

(30) Foreign Application Priority Data
Dec. 4, 2013    (EP) ...................................... 13195737

(51) Int. Cl.
| | | |
|---|---|---|
| *G01N 33/543* | (2006.01) | |
| *C09K 11/84* | (2006.01) | |
| *G01N 33/58* | (2006.01) | |
| *C08F 228/02* | (2006.01) | |
| *C09K 11/02* | (2006.01) | |
| *C09K 11/56* | (2006.01) | |
| *C09K 11/88* | (2006.01) | |

(52) U.S. Cl.
CPC .......... *C08F 228/02* (2013.01); *C09K 11/025* (2013.01); *C09K 11/565* (2013.01); *C09K 11/883* (2013.01); *G01N 33/54353* (2013.01); *G01N 33/587* (2013.01)

(58) Field of Classification Search
CPC ... C09K 11/025; C09K 11/565; C09K 11/883; G01N 33/54353; G01N 33/587; C08F 228/02
See application file for complete search history.

(56) References Cited

U.S. PATENT DOCUMENTS

2005/0277739 A1    12/2005    Yang et al.

OTHER PUBLICATIONS

Sun et al. Functionalization of quantum dots with multidentate zwitterionic ligands: impact on cellular interactions and cytotoxicity. J. of Materials Chemistry B, 2013, vol. 1, pp. 6137-6146. (Year: 2013).*
Yildiz et al. Hydrophilic CdSe—ZnS core-shell quantum dots with reactive functional groups on their surface. Langmuir 2010, vol. 26, No. 13, pp. 11503-11511. (Year: 2010).*
Chan, W et al., "Quantum Dot Bioconjugates for Ultrasensitive Nonisotopic Detection", Science, vol. 281, No. 5385, Sep. 1998, pp. 2016-2018.
Mattoussi, H et al., "Self-Assembly of CdSe—ZnS Quantum Dot Bioconjugates Using an Engineered Recombinant Protein", Journal of the American Chemical Society, vol. 122, No. 49, Nov. 2000, pp. 12142-12150.
Giovanelli, E et al., "Highly enhanced affinity of multidentate versus bidentate zwitterionic ligands for long-term quantum dot bioimaging", Langmuir, vol. 28, No. 43, Sep. 2012, pp. 15177-15184.
Chen, X et al., "Novel zwiterrionic copolymers with diohydrolipoic acid: synthesis and preparartion of nonfouling nanorods", Macromoelcules, vol. 46, No. 1, Dec. 2012, pp. 119-127.
Yildiz, I et al., "Hydrophilic CdSe—ZnS core shell quantum dots with reactive functional groups on their surface", Langmuir, vol. 26, No. 13, Jul. 2010, pp. 11503-11511.
European Search Report, from corresponding European Appln. No. EP13195737, dated Apr. 24, 2014.
International Search Report, from corresponding PCT Appln. No. PCT/EP2014/076655, dated Jan. 8, 2015.

* cited by examiner

*Primary Examiner* — Shafiqul Haq
(74) *Attorney, Agent, or Firm* — Young & Thompson

(57) ABSTRACT

Disclosed are functionalizable ligands, nanoparticles, preferably nanocrystals, complexed with ligands and their use for bio-imaging. A nano material includes a nanoparticle and at least one copolymer ligand. A ligand which is a copolymer of general formula (I): H—P[(A)x-co-(B)y]n-L-R.

11 Claims, 4 Drawing Sheets

NANOPARTICLES COMPLEXED WITH FUNCTIONALIZABLE ENHANCED AFFINITY LIGANDS AND USE THEREOF

FIELD OF INVENTION

The present invention relates to functionalizable ligands, nanoparticles complexed with said ligands, preferably nanocrystals complexed with ligands, and their use for bio-imaging.

BACKGROUND OF INVENTION

Colloidal semiconductor nanoparticles, named "quantum dots" (QDs), are crystalline objects that exhibit specific fluorescence properties. Their absorption cross section is very large, they are bright and their emission spectra have a small full width half maximum, and a peak wavelength that is tunable as a function of their composition, their size and their shape (in the range of a few nanometers to few tens of nanometers). They are also far more resistant to photobleaching than traditional organic dyes. These unique features make them very attractive for diverse applications in the field of medical and biological imaging, such as individual proteins monitoring, multi-color immunostaining, stem cells tracking, fluorescence acquisition cell sorting, or optically assisted surgery.

Functionalization of QDs surface presents many advantages. Especially, a second imaging agent may be coupled at the surface of the QD, to enable bimodal imaging. On another hand, functionalizing QDs' surface by coupling bio-targeting moieties is interesting for bio-imaging. Functionalization by a therapeutically active molecule may also be interesting.

QD syntheses provide colloidal solutions of fluorescent nanocrystals capped with ligands. Functionalization of QD may thus be performed by functionalizing ligands presents at their surface.

Typical QD syntheses provide QDs capped with hydrophobic ligands, while the use of QDs in live-cell imaging requires their complete solubility in water as well as an excellent compatibility with biological media. To make the QDs water-soluble, one method is to perform cap exchange, consisting in the replacement of original ligands by hydrophilic ones, bearing a chemical function able to bind to the nanocrystal surface (Chan et al. Science 1998, 281:2016 and Mattoussi et al. J. Am. Chem. Soc. 2000, 122:12142). Cap exchange results in small and stable QDs. The non-specific interactions of the QD with cell membranes or with biomolecules in general depend mainly on the moieties that are adsorbed on the QD surface. Ligand exchange provides a versatile method to control the size, the nature of the ligand as well as its affinity for the QD surface (ligands that are too strong can indeed dissolve the QD, while ligands that are not strong enough can detach from the QD surface).

Ligand desorption is a strong limitation for the use of QDs in bio-imaging. This desorption, favored in high diluted conditions, causes indeed a loss of colloidal stability and functionality, as well as an increase in aggregation and non-specific adsorption. As a consequence, continued efforts have been made to improve the affinity of passivating ligands for the QD surface. The design of these replacing ligands is also guided by further needs for biological applications of quantum dots, namely: small size; stability over a large pH range, at elevated salt concentrations and in a cellular medium; low non-specific adsorption; and possible functionalization afterwards.

To match the above-mentioned criteria, especially limitation of ligand desorption and provision of small and stable QDs, the Applicant developed a multidentate zwitterionic ligand L2, issued from the copolymerization of a bidentate monomer and a monozwitterionic monomer (Scheme 1) (Giovanelli et al. Langmuir 2012, 28, 15177-15184).

Scheme 1. Chemical structure of ligand L2.

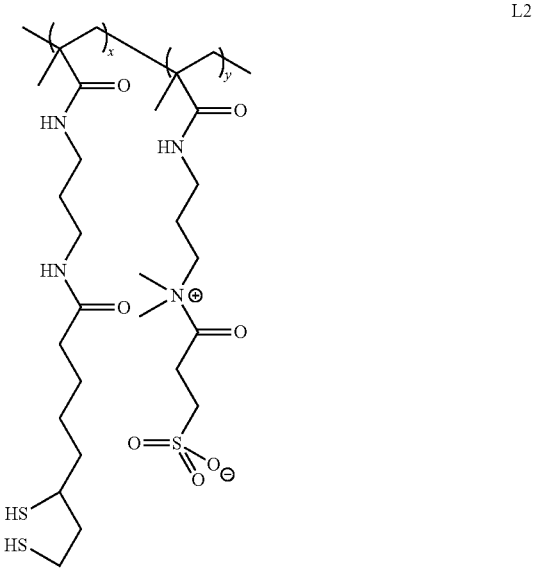

The structure of the lateral chains of L2 was evidenced to enhance affinity of this ligand toward QDs and thus avoid ligand desorption while keeping a small size of particle.

Derivatives of L2, L2-$NH_2$ and $L_2$-PEG-$NH_2$ were also proposed to introduce functionalizable amine later chains (scheme 2):

Scheme 2. Chemical structure of ligand L2—$NH_2$ and L2—PEG—$NH_2$.

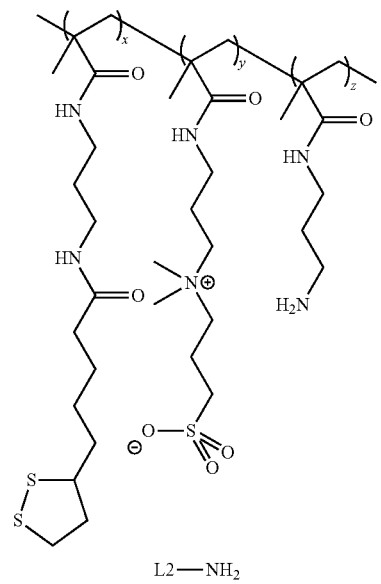

L2—$NH_2$

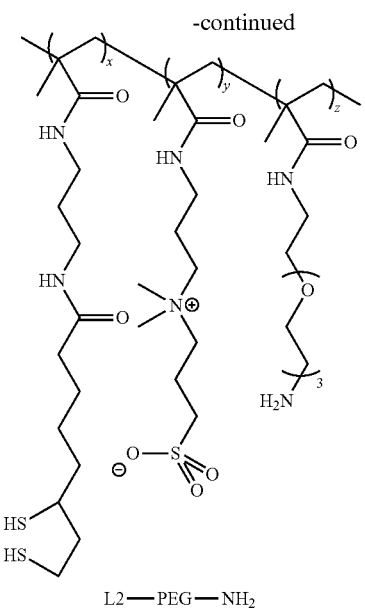

L2—PEG—NH$_2$

Especially, QD functionalization was performed for L2-NH$_2$ by conjugation with fluorescein. L2-PEG-NH$_2$-capped QDs were also conjugated via their amine function, with either biotin or avidin by peptidic coupling after capping QD.

Therefore, the Applicant provided a first generation of hydrophilic ligands having a very good affinity for QD and being functionalizable. However, with this first generation of ligands, functionalization requires to use at least three different monomers to form the ligand: an anchoring monomer, an hydrophilic monomer and a functionalizable monomer. Therefore, the resulting ligand is quite complex. Moreover, it was evidenced that functionalization of this type of ligand modifies its anchoring properties and therefore modifies the stability of the QD.

Therefore, there is a need for more simple ligands which remain functionalizable and for which functionalization does not modify anchoring properties.

The Applicant surprisingly showed that anchoring moieties of L2 ligand may be labile. If there is a sufficient number of anchoring functions in the ligand, a part of them is not linked to the surface of the QD and they may be used for functionalizing the ligand, without decreasing the anchoring stability. This presents the advantage of not requiring a modification of the ligand by a third functionalizable monomer. There is only the need to control the length of the ligand to ensure that there is a sufficient number of anchoring monomers to achieved both anchoring and functionalization.

Moreover, the Applicant evidenced that the ligand of the invention, which may be synthesized by radical polymerization in presence of CTA (chain transfer agent), bears one functionalizable end. Indeed, it was surprisingly shown that upon CTA polymerization, ligands bearing at the first end a hydrogen atom and at the other end the CTA were predominantly obtained, whereas numerous possibilities were expected for ends of the polymeric chain.

By varying the CTA to obtain a functionalizable end of the ligand and by selecting the anchoring moiety of the anchoring monomer, orthogonal functionalization of the ligand may be envisaged to introduce 2 types of functional groups on the ligand and thus on the QD. In this case, a first functional group may be introduced at one end of the ligand, while a second functional group may be introduced on some on the anchoring moieties on lateral chains.

Therefore, the Applicant herein provides a new ligand of QDs, which is a copolymer obtained from at least 2 monomers, said monomers being:
one anchoring monomer A having a side-chain comprising a first moiety $M_A$ having affinity for the surface of a nanocrystal, and
one hydrophilic monomer B having a side-chain comprising a second moiety $M_B$ being hydrophilic,
wherein one end of the copolymer is a hydrogen atom and the other end comprises a functionalizable group.

The functionalizable ligand of the invention presents the advantage that even coated on QDs, functionalizable end groups of the polymer are accessible to conjugation. Therefore, the ligand may be functionalized after complexation of QD.

SUMMARY

This invention thus relates to a nanomaterial comprising:
a nanoparticle, preferably a nanocrystal; and
at least one ligand which is a copolymer of formula (I)

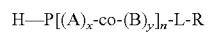

wherein
A represents an anchoring monomer having a side-chain comprising a first moiety $M_A$ having affinity for the surface of a nanocrystal;
B represents a hydrophilic monomer having a side-chain comprising a second moiety $M_B$ being hydrophilic;
n represents a positive integer, preferably an integer ranging from 1 to 1000, preferably from 1 to 499, from 1 to 249 or from 1 to 99;
x and y represent each independently a percentage of n, wherein x and y are different from 0% of n and different from 100% of n, preferably ranging from more than 0% to less than 100% of n, preferably from more than 0% to 80% of n, from more than 0% to 50% of n; wherein x+y is equal to 100% of n;
R represents:
a functional group selected from the group comprising —NH$_2$, —COOH, —OH, —SH, —CHO, ketone, halide; activated ester such as for example N-hydroxysuccinimide ester, N-hydroxyglutarimide ester or maleimide ester; activated carboxylic acid such as for example acid anhydride or acid halide; isothiocyanate; isocyanate; alkyne; azide; glutaric anhydride, succinic anhydride, maleic anhydride; hydrazide; chloroformate, maleimide, alkene, silane, hydrazone, oxime and furan;
a bioactive group selected from the group comprising avidin or streptavidin; antibody such as a monoclonal antibody or a single chain antibody; sugars; a protein or peptide sequence having a specific binding affinity for an affinity target, such as for example an avimer or an affibody (the affinity target may be for example a protein, a nucleic acid, a peptide, a metabolite or a small molecule), antigens, steroids, vitamins, drugs, haptens, metabolites, toxins, environmental pollutants, amino acids, peptides, proteins, aptamers, nucleic acids, nucleotides, peptide nucleic acid (PNA), folates, carbohydrates, lipids, phospholipid, lipoprotein, lipopolysaccharide, liposome hormone, polysaccharide, polymers, polyhistidine tags, fluorophores; and L represents a bound or a spacer selected from the group comprising alkylene, alkenylene, arylene or arylalkyl linking groups having 1 to 50 chain atoms, wherein the linking group can be optionally interrupted or terminated by —O—, —S—, —NR$_7$—, wherein R$_7$ is H or alkyl, —CO—, —NHCO—, —CONH— or a combination thereof; or a spacer selected from the group comprising DNA, RNA, peptide nucleic acid (PNA), polysaccharide, peptide.

According to one embodiment, in the nanomaterial of the invention, the nanoparticle is a nanocrystal and the nanocrystal is a 0D, 1D, or 2D nanocrystal, preferably a nanosheet, a nanorod, a nanoplatelet, a nanoplate, a nanoprism, a nanowall, a nanodisk, a nanoparticle, a nanowire, a nanopowder, a nanotube, a nanotetrapod, a nanoribbon, a nanobelt, a nanoneedle, a nanocube, a nanoball, a nanocoil, a nanocone, a nanopiller, a nanoflower, or a quantum dot.

According to one embodiment, in the nanomaterial of the invention, the ligand is of formula (II):

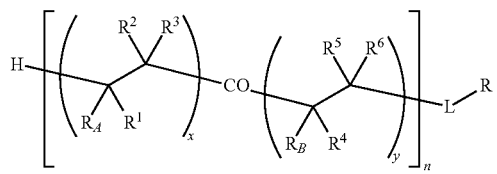

wherein
n, x, y, L and R are as defined above;
R$_A$ represents a group comprising the first moiety M$_A$ having affinity for the surface of a nanocrystal;
R$_B$ represents a group comprising the second moiety M$_B$ being hydrophilic;
R$^1$, R$^2$, R$^3$, R$^4$, R$^5$ and R$^6$ represent each independently H or a group selected from the alkyl, alkenyl, aryl, hydroxyl, halogen, alkoxy and carboxylate, amide.

According to one embodiment, in the nanomaterial of the invention, the ligand is of formula (I-e'):

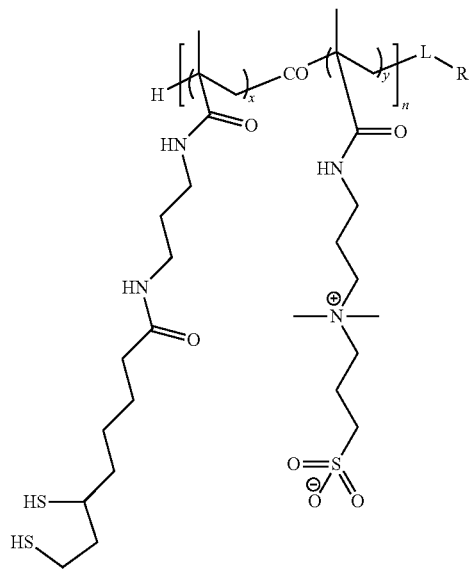

wherein n, x, y, L and R are as defined above.

According to one embodiment, in the nanomaterial of the invention, the ligand is of formula (I-f'):

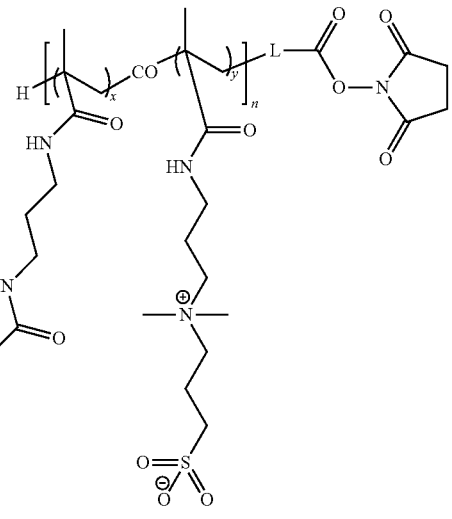

wherein n, x, y and L are as defined above.

The invention further relates to a ligand which is a copolymer of general formula (I):

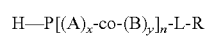

wherein
A represents an anchoring monomer having a side-chain comprising a first moiety M$_A$ having affinity for the surface of a nanocrystal;
B represents a hydrophilic monomer having a side-chain comprising a second moiety M$_B$ being hydrophilic;
n represents a positive integer, preferably an integer ranging from 1 to 1000, preferably from 1 to 499, from 1 to 249 or from 1 to 99;
x and y represent each independently a percentage of n, wherein x and y are different from 0% of n and different from 100% of n, preferably ranging from more than 0% to less than 100% of n, preferably from more than 0% to 80% of n, from more than 0% to 50% of n; wherein x+y is equal to 100% of n;
R represents:
a functional group selected from the group comprising —NH$_2$, —COOH, —OH, —SH, —CHO, ketone, halide; activated ester such as for example N-hydroxysuccinimide ester, N-hydroxyglutarimide ester or maleimide ester; activated carboxylic acid such as for example acid anhydride or acid halide; isothiocyanate; isocyanate; alkyne; azide; glutaric anhydride, succinic anhydride, maleic anhydride; hydrazide; chloroformate, maleimide, alkene, silane, hydrazone, oxime and furan; and
a bioactive group selected from the group comprising avidin or streptavidin; antibody such as a monoclonal antibody or a single chain antibody; sugars; a protein or peptide sequence having a specific binding affinity for an affinity target, such as for example an avimer or an affibody (the affinity target may be for example a protein, a nucleic acid, a peptide, a metabolite or a small molecule), antigens, steroids, vitamins, drugs, haptens, metabolites, toxins, environmental pollutants, amino acids, peptides, proteins, aptamers, nucleic acids, nucleotides, peptide nucleic acid (PNA), folates, carbohydrates, lipids, phospholipid, lipoprotein, lipopolysaccharide, liposome hormone, polysaccharide, polymers, polyhistidine tags, fluorophores; and L represents a bound or a spacer selected from the group comprising alkylene, alkenylene, arylene or arylalkyl linking groups having 1 to 50 chain atoms, wherein the linking group can be optionally interrupted or terminated by —O—, —S—, —NR$_7$—, wherein R$_7$ is H or alkyl, —CO—, —NHCO—, —CONH— or a combination thereof; or a spacer selected from the group comprising DNA, RNA, peptide nucleic acid (PNA), polysaccharide, peptide.

According to one embodiment, the ligand of the invention is of general formula (II):

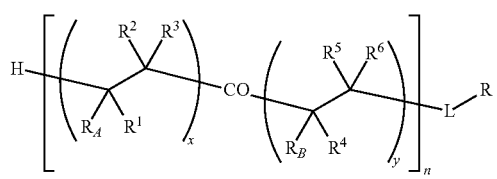

wherein n, x, y, L and R are as defined above;

R$_A$ represents a group comprising the first moiety M$_A$ having affinity for the surface of a nanocrystal;

R$_B$ represents a group comprising the second moiety M$_B$ being hydrophilic;

R$^1$, R$^2$, R$^3$, R$^4$, R$^5$ and R$^6$ represent each independently H or a group selected from the alkyl, alkenyl, aryl, hydroxyl, halogen, alkoxy and carboxylate, amide.

According to one embodiment, the ligand of the invention is of formula (I-e):

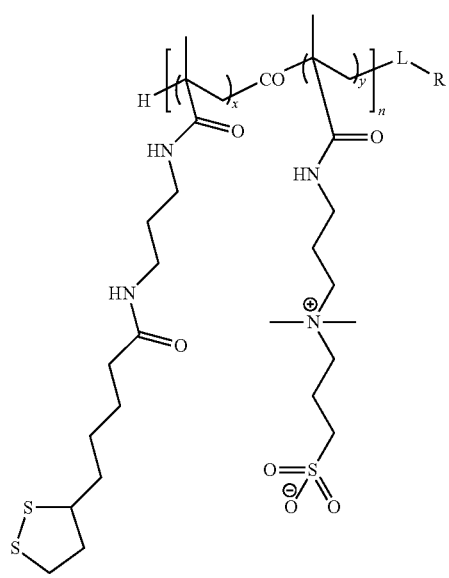

wherein n, x, y, L and R are as defined above.

According to one embodiment, the ligand of the invention is of formula (I-f):

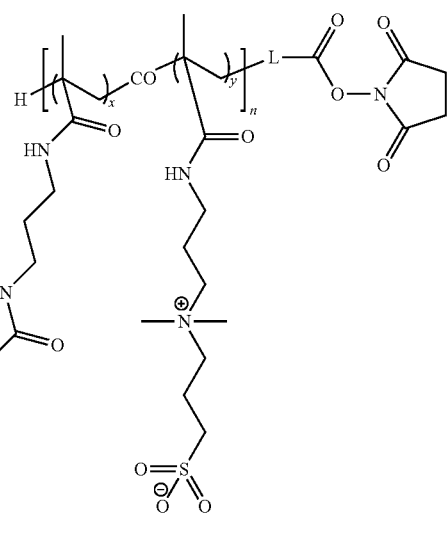

wherein n, x, y and L are as defined above.

According to one embodiment, in the ligand of the invention, L represents an alkylene linking group having 1 to 20 chain atoms and optionally interrupted or terminated by —O— or —S—.

According to one embodiment, in the ligand of the invention, R represents —COOH or —NH$_2$.

The invention also relates to a water-soluble composition comprising nanomaterials according to the invention.

The present invention further relates to the use of a nanomaterial according to the invention or of the water-soluble composition according to the invention for bioimaging, biotargeting, medical imaging or biosensing.

The invention also relates to a method for manufacturing the ligand according the invention comprising polymerizing an anchoring monomer A and a hydrophilic monomer B in presence of an initiator and a chain transfer agent (CTA), wherein anchoring monomer A and a hydrophilic monomer B are as defined above.

The present invention further relates to a method for manufacturing the nanomaterial according to the invention comprising:
  optionally a first step of complexation of nanocrystals with an intermediate ligand being a weakly binding ligand or a small molecule ensuring the homogeneous dispersion of the nanocrystal into a solvent miscible in part with water;
  a step of monophasic exchange at about 40° C. to about 100° C. in an aqueous medium overnight to remove the weak intermediate ligand and replace it by the ligand according to the invention;
  optionally one or more subsequent steps selected from:
    in the case wherein R represents a functional group in the ligand of formula (I), a step of bio-conjugation to introduce a bioactive group at the end of the polymeric chain of the ligand;
    functionalization of some of the M$_A$ moieties of the anchoring monomers A of the ligand by bioactive groups.

Definitions

In the present invention, the following terms have the following meanings:

"chain-transfer agent" refers to a substance able to react 1) either with a radical initiator during a polymerization reaction and the radical active center is transferred from the initiator to said substance, allowing said substance to initiate another radical (co)polymerization, or 2) said substance may react with a growing macromolecular chain during a polymerization reaction allowing transferring the radical active center from the growing chain to said substance and thus allowing said substance the initiation of another radical (co)polymerization.

"functional group" refers to a group selected from —$NH_2$, —COOH, —OH, —SH, —CHO, ketone, halide; activated ester such as for example N-hydroxysuccinimide ester, N-hydroxyglutarimide ester or maleimide ester; activated carboxylic acid such as for example acid anhydride or acid halide; isothiocyanate; isocyanate; alkyne; azide; glutaric anhydride, succinic anhydride, maleic anhydride; hydrazide; chloroformate, maleimide, alkene, silane, hydrazone, oxime and furan.

"bioactive group" refers to a chemical group suitable to induce site-specific delivery of the compound once administered. In a preferred embodiment of the invention, the bioactive group is selected from the group comprising avidin or streptavidin; antibody such as a monoclonal antibody or a single chain antibody; sugars; a protein or peptide sequence having a specific binding affinity for an affinity target, such as for example an avimer or an affibody (the affinity target may be for example a protein, a nucleic acid, a peptide, a metabolite or a small molecule), antigens, steroids, vitamins, drugs, haptens, metabolites, toxins, environmental pollutants, amino acids, peptides, proteins, aptamers, nucleotides, nucleic acids, folates, carbohydrates, lipids, phospholipid, lipoprotein, lipopolysaccharide, liposome hormone, polysaccharide, polymers, polyhistidine tags, fluorophores.

"alkyl" refers to any saturated linear or branched hydrocarbon chain, with 1 to 50 carbon atoms, preferably 1 to 6 carbon atoms, and more preferably methyl, ethyl, propyl, isopropyl, n-butyl, sec-butyl, isobutyl and tert-butyl. The alkyl group may be substituted by a saturated or unsaturated aryl group.

When the suffix "ene" ("alkylene") is used in conjunction with an alkyl group, this is intended to mean the alkyl group as defined herein having two single bonds as points of attachment to other groups. The term "alkylene" includes methylene, ethylene, methylmethylene, propylene, ethylethylene, and 1,2-dimethylethylene.

"alkenyl" refers to any linear or branched hydrocarbon chain having at least one double bond, of 2 to 50 carbon atoms, and preferably 2 to 6 carbon atoms. The alkenyl group may be substituted. Examples of alkenyl groups are ethenyl, 2-propenyl, 2-butenyl, 3-butenyl, 2-pentenyl and its isomers, 2-hexenyl and its isomers, 2,4-pentadienyl and the like. The alkenyl group may be substituted by a saturated or unsaturated aryl group.

"alkynyl" refers to any linear or branched hydrocarbon chain having at least one triple bond, of 2 to 50 carbon atoms, and preferably 2 to 6 carbon atoms.

The terms "alkenylene" means an alkenyl group as defined above having two single bonds as points of attachment to other groups.

"aryl" refers to a mono- or polycyclic system of 5 to 20, and preferably 6 to 12, carbon atoms having one or more aromatic rings (when there are two rings, it is called a biaryl) among which it is possible to cite the phenyl group, the biphenyl group, the 1-naphthyl group, the 2-naphthyl group, the tetrahydronaphthyl group, the indanyl group and the binaphthyl group. The term aryl also means any aromatic ring including at least one heteroatom chosen from an oxygen, nitrogen or sulfur atom. The aryl group can be substituted by 1 to 3 substituents chosen independently of one another, among a hydroxyl group, a linear or branched alkyl group comprising 1, 2, 3, 4, 5 or 6 carbon atoms, in particular methyl, ethyl, propyl, butyl, an alkoxy group or a halogen atom, in particular bromine, chlorine and iodine, a nitro group, a cyano group, an azido group, an adhehyde group, a boronato group, a phenyl, $CF_3$, methylenedioxy, ethylenedioxy, $SO_2NRR'$, NRR', COOR (where R and R' are each independently selected from the group consisting of H and alkyl), an second aryl group which may be substituted as above. Non-limiting examples of aryl comprise phenyl, biphenylyl, biphenylenyl, 5- or 6-tetralinyl, naphthalen-1- or -2-yl, 4-, 5-, 6 or 7-indenyl, 1- 2-, 3-, 4- or 5-acenaphtylenyl, 3-, 4- or 5-acenaphtenyl, 1- or 2-pentalenyl, 4- or 5-indanyl, 5-, 6-, 7- or 8-tetrahydronaphthyl, 1,2,3,4-tetrahydronaphthyl, 1,4-dihydronaphthyl, 1-, 2-, 3-, 4- or 5-pyrenyl.

The term "arylene" as used herein is intended to include divalent carbocyclic aromatic ring systems such as phenylene, biphenylylene, naphthylene, indenylene, pentalenylene, azulenylene and the like.

"cycle" refers to a saturated, partially unsaturated or unsaturated cyclic group.

"heterocycle" refers to a saturated, partially unsaturated or unsaturated cyclic group comprising at least on heteroatom.

"halogen" means fluoro, chloro, bromo, or iodo. Preferred halo groups are fluoro and chloro.

"alkoxy" refers to any O-alkyl group, preferably an O-alkyl group wherein the alkyl group has 1 to 6 carbon atoms.

"aryloxy" refers to any O-aryl group.

"arylalkyl" refers to an alkyl group substituted by an aryl group, such as for example the phenyl-methyl group.

"arylalkoxy" refers to an alkoxy group substituted by an aryl group.

"amine" refers to any group derived from ammoniac $NH_3$ by substitution of one or more hydrogen atoms with an organic radical.

"azido" refers to —$N_3$ group.

"acidic function" refers to —COOH group.

"activated acidic function" refers to an acidic function wherein the —OH is replaced by a better leaving group.

"activated alcoholic function" refers to an alcoholic function modified to be a better leaving group.

"hydrophilic" refers to a molecule or portion of a molecule that has a tendency to interact with or be dissolved by water and other polar substances.

DETAILED DESCRIPTION

The present invention relates to a ligand which is a copolymer obtained from at least 2 monomers, said monomers being:
one anchoring monomer A having a side-chain comprising a first moiety $M_A$ having affinity for the surface of a material; and
one hydrophilic monomer B having a side-chain comprising a second moiety $M_B$ being hydrophilic;
and wherein one end of copolymer is H and the other end comprises a functional group or a bioactive group.

In one embodiment, the material for which the first moiety $M_A$ has affinity, is selected from the group comprising metals, semiconductors, oxides, lanthanides or mixtures thereof.

In one embodiment, the material is preferably selected from gold, iron, silver, copper, aluminum, platinum, lead, palladium, iron oxide, titanium dioxide, cerium oxide, metal chalcogenide, metal pnictide, cadmium, zinc, magnesium, mercury, gallium, indium, thallium, cobalt, tin or mixtures thereof.

In a specific embodiment, the material for which the first moiety $M_A$ has affinity, is under the form of particles, preferably nanoparticles. According to one embodiment, nanoparticles may be nanocrystals.

Especially, the present invention relates to a ligand which is a copolymer obtained from at least 2 monomers, said monomers being:
- one anchoring monomer A having a side-chain comprising a first moiety $M_A$ having affinity for the surface of a nanocrystal; and
- one hydrophilic monomer B having a side-chain comprising a second moiety $M_B$ being hydrophilic;

and wherein one end of copolymer is H and the other end comprises a functional group or a bioactive group.

According to one embodiment, the functional group is selected from the group comprising —NH₂, —COOH, —OH, —SH, —CHO, ketone, halide; activated ester such as for example N-hydroxysuccinimide ester, N-hydroxyglutarimide ester or maleimide ester; activated carboxylic acid such as for example acid anhydride or acid halide; isothiocyanate; isocyanate; alkyne; azide; glutaric anhydride, succinic anhydride, maleic anhydride; hydrazide; chloroformate, maleimide, alkene, silane, hydrazone, oxime and furan.

According to an embodiment, the bioactive group is selected from the group comprising avidin or streptavidin; antibody such as a monoclonal antibody or a single chain antibody; sugars; a protein or peptide sequence having a specific binding affinity for an affinity target, such as for example an avimer or an affibody (the affinity target may be for example a protein, a nucleic acid, a peptide, a metabolite or a small molecule), antigens, steroids, vitamins, drugs, haptens, metabolites, toxins, environmental pollutants, amino acids, peptides, proteins, aptamers, nucleic acids, nucleotides, peptide nucleic acid (PNA), folates, carbohydrates, lipids, phospholipid, lipoprotein, lipopolysaccharide, liposome hormone, polysaccharide, polymers, polyhistidine tags, fluorophores.

In an embodiment of the invention monomers A and B are methacrylamide monomers.

In one embodiment, the first moiety $M_A$ having affinity for the surface of a nanocrystal has preferably affinity for a metal present at the surface of a nanocrystal or for a material E present at the surface of a nanocrystal and selected in the group of O, S, Se, Te, N, P, As, and mixture thereof.

Examples of metal present at the surface of a nanocrystal include, but are not limited to, gold, iron oxide, titanium dioxide, cerium oxide, metal chalcogenide, metal pnictide, cadmium, zinc, magnesium, mercury, aluminium, gallium, indium, thallium, copper, cobalt, platinum, silver, tin, lead and mixtures thereof.

In one embodiment, the ligand of the invention is a copolymer having a plurality of monomers including monomer A and monomer B. In one embodiment, said ligand is a random, alternate or block copolymer. In another embodiment, the ligand is a statistic copolymer. In another embodiment, said ligand is a random or block copolymer consisting essentially of monomer A and monomer B. In one embodiment of the invention, said ligand is a multi-dentate ligand.

According to one embodiment, preferred monomers A are those described in the following table:

| Compound n° | Name |
|---|---|
| A1 | 5-(1,2-dithiolan-3-yl)-N-(3-methacrylamidopropyl)pentanamide |
| A2 | 6-(1,2-dithiolan-3-yl)-N-(3-methacrylamidopropyl)hexanamide |
| A3 | 7-(1,2-dithiolan-3-yl)-N-(3-methacrylamidopropyl)heptanamide |
| A4 | 8-(1,2-dithiolan-3-yl)-N-(3-methacrylamidopropyl)octanamide |
| A5 | 9-(1,2-dithiolan-3-yl)-N-(3-methacrylamidopropyl)nonanamide |
| A6 | 10-(1,2-dithiolan-3-yl)-N-(3-methacrylamidopropyl)decanamide |
| A7 | 5-(1,2-dithiolan-3-yl)-N-(3-acrylamidopropyl)pentanamide |
| A8 | 6-(1,2-dithiolan-3-yl)-N-(3-acrylamidopropyl)hexanamide |
| A9 | 7-(1,2-dithiolan-3-yl)-N-(3-acrylamidopropyl)heptanamide |
| A10 | 8-(1,2-dithiolan-3-yl)-N-(3-acrylamidopropyl)octanamide |
| A11 | 9-(1,2-dithiolan-3-yl)-N-(3-acrylamidopropyl)nonanamide |
| A12 | 10-(1,2-dithiolan-3-yl)-N-(3-acrylamidopropyl)decanamide |
| A13 | 3-(5-(1,2-dithiolan-3-yl)pentanamido)propyl methacrylate |
| A14 | 3-(6-(1,2-dithiolan-3-yl)hexanamido)propyl methacrylate |
| A15 | 3-(7-(1,2-dithiolan-3-yl)heptanamido)propyl methacrylate |
| A16 | 3-(8-(1,2-dithiolan-3-yl)octanamido)propyl methacrylate |
| A17 | 3-(9-(1,2-dithiolan-3-yl)nonanamido)propyl methacrylate |
| A18 | 3-(10-(1,2-dithiolan-3-yl)decanamido)propyl methacrylate |
| A19 | 3-(11-(1,2-dithiolan-3-yl)pentanamido)propyl acrylate |
| A20 | 3-(6-(1,2-dithiolan-3-yl)hexanamido)propyl acrylate |
| A21 | 3-(7-(1,2-dithiolan-3-ylheptamido)propyl acrylate |
| A22 | 3-(8-(1,2-dithiolan-3-yl)octanamido)propyl acrylate |
| A23 | 3-(9-(1,2-dithiolan-3-yl)nonanamido)propyl acrylate |
| A24 | 3-(10-(1,2-dithiolan-3-yl)decanamido)propyl acrylate |
| A25 | 5-mercapto-N-(3-methacrylamidopropyl)pentanamide |
| A26 | 6-mercapto-N-(3-methacrylamidopropyl)hexanamide |
| A27 | 7-mercapto-N-(3-methacrylamidopropyl)heptanamide |
| A28 | 8-mercapto-N-(3-methacrylamidopropyl)octanamide |
| A29 | 9-mercapto-N-(3-methacrylamidopropyl)nonanamide |
| A30 | 10-mercapto-N-(3-methacrylamidopropyl)decanamide |
| A31 | N-(3-acrylamidopropyl)-5-mercaptopentanamide |
| A32 | N-(3-acrylamidopropyl)-6-mercaptohexanamide |
| A33 | N-(3-acrylamidopropyl)-7-mercaptoheptanamide |
| A34 | N-(3-acrylamidopropyl)-8-mercaptooctanamide |
| A35 | N-(3-acrylamidopropyl)-9-mercaptononanamide |
| A36 | N-(3-acrylamidopropyl)-10-mercaptodecanamide |
| A37 | 3-(5-mercaptopentanamido)propyl methacrylate |
| A38 | 3-(6-mercaptohexanamido)propyl methacrylate |
| A39 | 3-(7-mercaptoheptanamido)propyl methacrylate |
| A40 | 3-(8-mercaptooctanamido)propyl methacrylate |
| A41 | 3-(9-mercaptononanamido)propyl methacrylate |
| A42 | 3-(10-mercaptodecanamido)propyl methacrylate |
| A43 | 3-(5-mercaptopentanamido)propyl acrylate |
| A44 | 3-(6-mercaptohexanamido)propyl acrylate |
| A45 | 3-(7-mercaptoheptanamido)propyl acrylate |
| A46 | 3-(8-mercaptooctanamido)propyl acrylate |
| A47 | 3-(9-mercaptononanamido)propyl acrylate |
| A48 | 3-(10-mercaptodecanamido)propyl acrylate |
| A49 | 5-((3-methacrylamidopropyl)amino)-5-oxopentanoic acid |
| A50 | 6-((3-methacrylamidopropyl)amino)-6-oxohexanoic acid |
| A51 | 7-((3-methacrylamidopropyl)amino)-7-oxoheptanoic acid |
| A52 | 8-((3-methacrylamidopropyl)amino)-8-oxooctanoic acid |
| A53 | 9-((3-methacrylamidopropyl)amino)-9-oxononanoic acid |
| A54 | 10-((3-methacrylamidopropyl)amino)-10-oxodecanoic acid |
| A55 | 5-((3-acrylamidopropyl)amino)-5-oxopentanoic acid |
| A56 | 6-((3-acrylamidopropyl)amino)-6-oxohexanoic acid |
| A57 | 7-((3-acrylamidopropyl)amino)-7-oxoheptanoic acid |
| A58 | 8-((3-acrylamidopropyl)amino)-8-oxooctanoic acid |
| A59 | 9-((3-acrylamidopropyl)amino)-9-oxononanoic acid |
| A60 | 10-((3-acrylamidopropyl)amino)-10-oxodecanoic acid |
| A61 | 5-((3-(methacryloyloxy)propyl)amino)-5-oxopentanoic acid |
| A62 | 6-((3-(methacryloyloxy)propyl)amino)-6-oxohexanoic acid |
| A63 | 7-((3-(methacryloyloxy)propyl)amino)-7-oxoheptanoic acid |
| A64 | 8-((3-(methacryloyloxy)propyl)amino)-8-oxooctanoic acid |
| A65 | 9-((3-(methacryloyloxy)propyl)amino)-9-oxononanoic acid |
| A66 | 10-((3-(methacryloyloxy)propyl)amino)-10-oxodecanoic acid |
| A67 | 5-((3-(acryloyloxy)propyl)amino)-5-oxopentanoic acid |
| A68 | 6-((3-(acryloyloxy)propyl)amino)-6-oxohexanoic acid |
| A69 | 7-((3-(acryloyloxy)propyl)amino)-7-oxoheptanoic acid |
| A70 | 8-((3-(acryloyloxy)propyl)amino)-8-oxooctanoic acid |
| A71 | 9-((3-(acryloyloxy)propyl)amino)-9-oxononanoic acid |
| A72 | 10-((3-(acryloyloxy)propyl)amino)-10-oxodecanoic acid |

-continued

| Compound n° | Name |
|---|---|
| A73 | 5-amino-N-(3-methacrylamidopropyl)pentanamide |
| A74 | 6-amino-N-(3-methacrylamidopropyl)hexanamide |
| A75 | 7-amino-N-(3-methacrylamidopropyl)heptanamide |
| A76 | 8-amino-N-(3-methacrylamidopropyl)octanamide |
| A77 | 9-amino-N-(3-methacrylamidopropyl)nonanamide |
| A78 | 10-amino-N-(3-methacrylamidopropyl)decanamide |
| A79 | N-(3-acrylamidopropyl)-5-aminopentanamide |
| A80 | N-(3-acrylamidopropyl)-6-aminohexanamide |
| A81 | N-(3-acrylamidopropyl)-7-aminheptanamide |
| A82 | N-(3-acrylamidopropyl)-8-aminooctanamide |
| A83 | N-(3-acrylamidopropyl)-9-aminononanamide |
| A84 | N-(3-acrylamidopropyl)-10-aminodecanamide |
| A85 | 3-(5-aminopentanamido)propyl methacrylate |
| A86 | 3-(6-aminohexanamido)propyl methacrylate |
| A87 | 3-(7-aminoheptanamido)propyl methacrylate |
| A88 | 3-(8-aminooctanamido)propyl methacrylate |
| A89 | 3-(9-aminononamido)propyl methacrylate |
| A90 | 3-(10-aminodecanamido)propyl methacrylate |
| A91 | 3-(5-aminopentanamido)propyl acrylate |
| A92 | 3-(6-aminohexanamido)propyl acrylate |
| A93 | 3-(7-aminoheptanamido)propyl acrylate |
| A94 | 3-(8-aminooctanamido)propyl acrylate |
| A95 | 3-(9-aminononamido)propyl acrylate |
| A96 | 3-(10-aminodecanamido)propyl acrylate |

According to one embodiment, preferred monomers B are those described in the following table:

| Compound n° | Name |
|---|---|
| B1 | 3-((3-methacrylamidopropyl)dimethylammonio)propane-1-sulfonate |
| B2 | 5-((3-methacrylamidopropyl)dimethylammonio)pentane-1-sulfonate |
| B3 | 6-((3-methacrylamidopropyl)dimethylammonio)hexane-1-sulfonate |
| B4 | 7-((3-methacrylamidopropyl)dimethylammonio)heptane-1-sulfonate |
| B5 | 8-((3-methacrylamidopropyl)dimethylammonio)octane-1-sulfonate |
| B6 | 9-((3-methacrylamidopropyl)dimethylammonio)nonane-1-sulfonate |
| B7 | 10-((3-methacrylamidopropyl)dimethylammonio)décane-1-sulfonate |
| B8 | 3-((4-methacrylamidobutyl)dimethylammonio)propane-1-sulfonate |
| B9 | 3-((5-methacrylamidopentyl)dimethylammonio)propane-1-sulfonate |
| B10 | 3-((6-methacrylamidohexyl)dimethylammonio)propane-1-sulfonate |
| B11 | 3-((7-methacrylamidoheptyl)dimethylammonio)propane-1-sulfonate |
| B12 | 3-((8-methacrylamidooctyl)dimethylammonio)propane-1-sulfonate |
| B13 | 3-((9-methacrylamidononyl)dimethylammonio)propane-1-sulfonate |
| B14 | 3-((10-methacrylamidodecyl)dimethylammonio)propane-1-sulfonate |
| B15 | 3-((3-acrylamidopropyl)dimethylammonio)propane-1-sulfonate |
| B16 | 5-((3-acrylamidopropyl)dimethylammonio)pentane-1-sulfonate |
| B17 | 6-((3-acrylamidopropyl)dimethylammonio)hexane-1-sulfonate |
| B18 | 7-((3-acrylamidopropyl)dimethylammonio)heptane-1-sulfonate |
| B19 | 8-((3-acrylamidopropyl)dimethylammonio)octane-1-sulfonate |
| B20 | 9-((3-acrylamidopropyl)dimethylammonio)nonane-1-sulfonate |
| B21 | 10-((3-acrylamidopropyl)dimethylammonio)décane-1-sulfonate |
| B22 | 3-((4-acrylamidobutyl)dimethylammonio)propane-1-sulfonate |
| B23 | 3-((5-acrylamidopentyl)dimethylammonio)propane-1-sulfonate |
| B24 | 3-((6-acrylamidohexyl)dimethylammonio)propane-1-sulfonate |
| B25 | 3-((7-acrylamidoheptyl)dimethylammonio)propane-1-sulfonate |
| B26 | 3-((8-acrylamidooctyl)dimethylammonio)propane-1-sulfonate |
| B27 | 3-((9-acrylamidononyl)dimethylammonio)propane-1-sulfonate |
| B28 | 3-((10-acrylamidodecyl)dimethylammonio)propane-1-sulfonate |
| B29 | 3-((3-(methacryloyloxy)propyl)dimethylammonio)propane-1-sulfonate |
| B30 | 5-((3-(methacryloyloxy)propyl)dimethylammonio)pentane-1-sulfonate |
| B31 | 6-((3-(methacryloyloxy)propyl)dimethylammonio)hexane-1-sulfonate |
| B32 | 7-((3-(methacryloyloxy)propyl)dimethylammonio)heptane-1-sulfonate |
| B33 | 8-((3-(methacryloyloxy)propyl)dimethylammonio)octane-1-sulfonate |
| B34 | 9-((3-(methacryloyloxy)propyl)dimethylammonio)nonane-1-sulfonate |
| B35 | 10-((3-(methacryloyloxy)propyl)dimethylammonio)décane-1-sulfonate |
| B36 | 3-((4-(methacryloyloxy)butyl)dimethylammonio)propane-1-sulfonate |
| B37 | 3-((5-(methacryloyloxy)pentyl)dimethylammonio)propane-1-sulfonate |
| B38 | 3-((6-(methacryloyloxy)hexyl)dimethylammonio)propane-1-sulfonate |
| B39 | 3-((7-(methacryloyloxy)heptyl)dimethylammonio)propane-1-sulfonate |
| B40 | 3-((8-(methacryloyloxy)octyl)dimethylammonio)propane-1-sulfonate |
| B41 | 3-((9-(methacryloyloxy)nonyl)dimethylammonio)propane-1-sulfonate |
| B42 | 3-((10-(methacryloyloxy)decyl)dimethylammonio)propane-1-sulfonate |
| B43 | 3-((3-(acryloyloxy)propyl)dimethylammonio)propane-1-sulfonate |
| B44 | 5-((3-(acryloyloxy)propyl)dimethylammonio)pentane-1-sulfonate |
| B45 | 6-((3-(acryloyloxy)propyl)dimethylammonio)hexane-1-sulfonate |
| B46 | 7-((3-(acryloyloxy)propyl)dimethylammonio)heptane-1-sulfonate |
| B47 | 8-((3-(acryloyloxy)propyl)dimethylammonio)octane-1-sulfonate |
| B48 | 9-((3-(acryloyloxy)propyl)dimethylammonio)nonane-1-sulfonate |
| B49 | 10-((3-(acryloyloxy)propyl)dimethylammonio)décane-1-sulfonate |
| B50 | 3-((4-(acryloyloxy)butyl)dimethylammonio)propane-1-sulfonate |
| B51 | 3-((5-(acryloyloxy)pentyl)dimethylammonio)propane-1-sulfonate |
| B52 | 3-((6-(acryloyloxy)hexyl)dimethylammonio)propane-1-sulfonate |
| B53 | 3-((7-(methacryloyloxy)heptyl)dimethylammonio)propane-1-sulfonate |
| B54 | 3-((8-(acryloyloxy)octyl)dimethylammonio)propane-1-sulfonate |
| B55 | 3-((9-(acryloyloxy)nonyl)dimethylammonio)propane-1-sulfonate |
| B56 | 3-((10-(acryloyloxy)decyl)dimethylammonio)propane-1-sulfonate |
| B57 | 4-((3-methacrylamidopropyl)dimethylammonio)butanoate |
| B58 | 5-((3-methacrylamidopropyl)dimethylammonio)pentanoate |
| B59 | 6-((3-methacrylamidopropyl)dimethylammonio)hexanoate |
| B60 | 7-((3-methacrylamidopropyl)dimethylammonio)heptanoate |
| B61 | 8-((3-methacrylamidopropyl)dimethylammonio)octanoate |
| B62 | 9-((3-methacrylamidopropyl)dimethylammonio)nonanoate |

| Compound n° | Name |
|---|---|
| B63 | 10-((3-methacrylamidopropyl)dimethylammonio)decanoate |
| B64 | 4-((4-methacrylamidobutyl)dimethylammonio)butanoate |
| B65 | 4-((5-methacrylamidopentyl)dimethylammonio)butanoate |
| B66 | 4-((6-methacrylamidohexyl)dimethylammonio)butanoate |
| B67 | 4-((7-methacrylamidoheptyl)dimethylammonio)butanoate |
| B68 | 4-((8-methacrylamidooctyl)dimethylammonio)butanoate |
| B69 | 4-((9-methacrylamidononyl)dimethylammonio)butanoate |
| B70 | 4-((10-methacrylamidodecyl)dimethylammonio)butanoate |
| B71 | 4-(3-acrylamidopropyl)dimethylammonio)butanoate |
| B72 | 5-((3-acrylamidopropyl)dimethylammonio)pentanoate |
| B73 | 6-((3-acrylamidopropyl)dimethylammonio)hexanoate |
| B74 | 7-((3-acrylamidopropyl)dimethylammonio)heptanoate |
| B75 | 8-((3-acrylamidopropyl)dimethylammonio)octanoate |
| B76 | 9-((3-acrylamidopropyl)dimethylammonio)nonanoate |
| B77 | 10-((3-acrylamidopropyl)dimethylammonio)decanoate |
| B78 | 4-((4-acrylamidobutyl)dimethylammonio)butanoate |
| B79 | 4-((5-acrylamidopentyl)dimethylammonio)butanoate |
| B80 | 4-((6-acrylamidohexyl)dimethylammonio)butanoate |
| B81 | 4-((7-acrylamidoheptyl)dimethylammonio)butanoate |
| B82 | 4-(8-acrylamidooctyl)dimethylammonio)butanoate |
| B83 | 4-(9-acrylamidononyl)dimethylammonio)butanoate |
| B84 | 4-((10-acrylamidodecyl)dimethylammonio)butanoate |
| B85 | 4-((3-methacryloyloxypropyl)dimethylammonio)butanoate |
| B86 | 5-((3-methacryloyloxypropyl)dimethylammonio)pentanoate |
| B87 | 6-((3-methacryloyloxypropyl)dimethylammonio)hexanoate |
| B88 | 7-((3-methacryloyloxypropyl)dimethylammonio)heptanoate |
| B89 | 8-((3-methacryloyloxypropyl)dimethylammonio)octanoate |
| B90 | 9-((3-methacryloyloxypropyl)dimethylammonio)nonanoate |
| B91 | 10-((3-methacryloyloxypropyl)dimethylammonio)decanoate |
| B92 | 4-((4-methacryloyloxybutyl)dimethylammonio)butanoate |
| B93 | 4-((5-methacryloyloxypentyl)dimethylammonio)butanoate |
| B94 | 4-((6-methacryloyloxyhexyl)dimethylammonio)butanoate |
| B95 | 4-((7-methacryloyloxyheptyl)dimethylammonio)butanoate |
| B96 | 4-(9-methacryloyloxynonyl)dimethylammonio)butanoate |
| B97 | 4-((10-methacryloyloxydecyl)dimethylammonio)butanoate |
| B98 | 4-((3-acryloyloxypropyl)dimethylammonio)butanoate |
| B99 | 5-((3-acryloyloxypropyl)dimethylammonio)pentanoate |
| B100 | 6-((3-acryloyloxypropyl)dimethylammonio)hexanoate |
| B101 | 7-((3-acryloyloxypropyl)dimethylammonio)heptanoate |
| B102 | 8-((3-acryloyloxypropyl)dimethylammonio)octanoate |
| B103 | 9-((3-acryloyloxypropyl)dimethylammonio)nonanoate |
| B104 | 10-((3-acryloyloxypropyl)dimethylammonio)decanoate |
| B105 | 4-((4-acryloyloxybutyl)dimethylammonio)butanoate |
| B106 | 4-((5-acryloyloxypentyl)dimethylammonio)butanoate |
| B107 | 4-((6-acryloyloxyhexyl)dimethylammonio)butanoate |
| B108 | 4-((7-acryloyloxyheptyl)dimethylammonio)butanoate |
| B109 | 4-((9-acryloyloxynonyl)dimethylammonio)butanoate |
| B110 | 4-((10-acryloyloxydecyl)dimethylammonio)butanoate |

According to one embodiment, preferred -L-R are those described in the following table:

| Compound n° | Chemical structure |
|---|---|
| LR1 | —S—$(CH_2)_2$—(O—$CH_2$—$CH2)_8$—COOH |
| LR2 | —S—$(CH_2)_3$—(O—$CH_2$—$CH_2)_8$—COOH |
| LR3 | —S—$(CH_2)_4$—(O—$CH_2$—$CH_2)_8$—COOH |
| LR4 | —S—$(CH_2)_5$—(O—$CH_2$—$CH_2)_8$—COOH |
| LR5 | —S—$(CH_2)_6$—(O—$CH_2$—$CH_2)_8$—COOH |
| LR6 | —S—$(CH_2)_7$—(O—$CH_2$—$CH_2)_8$—COOH |
| LR7 | —S—$(CH_2)_8$—(O—$CH_2$—$CH_2)_8$—COOH |
| LR8 | —S—$(CH_2)_9$—(O—$CH_2$—$CH_2)_8$—COOH |
| LR9 | —S—$(CH_2)_{10}$—(O—$CH_2$—$CH_2)_8$—COOH |
| LR10 | —S—$(CH_2)_2$—(O—$CH_2$—$CH_2)_9$—COOH |
| LR11 | —S—$(CH_2)_2$—(O—$CH_2$—$CH_2)_{10}$—COOH |
| LR12 | —S—$(CH_2)_2$—(O—$CH_2$—$CH_2)_{11}$—COOH |
| LR13 | —S—$(CH_2)_2$—(O—$CH_2$—$CH_2)_{12}$—COOH |
| LR14 | —S—$(CH_2)_2$—(O—$CH_2$—$CH_2)_{13}$—COOH |
| LR15 | —S—$(CH_2)_2$—(O—$CH_2$—$CH_2)_{14}$—COOH |
| LR16 | —S—$(CH_2)_2$—(O—$CH_2$—$CH_2)_{15}$—COOH |
| LR17 | —S—$(CH_2)_2$—(O—$CH_2$—$CH_2)_{16}$—COOH |
| LR18 | —S—$(CH_2)_2$—(O—$CH_2$—$CH_2)_{17}$—COOH |
| LR19 | —S—$(CH_2)_2$—(O—$CH_2$—$CH_2)_{18}$—COOH |
| LR20 | —S—$(CH_2)_2$—(O—$CH_2$—$CH_2)_{19}$—COOH |
| LR21 | —S—$(CH_2)_2$—(O—$CH_2$—$CH_2)_{20}$—COOH |
| LR22 | —S—$(CH_2)_2$—(O—$CH_2$—$CH_2)_8$—CO—NHS |
| LR23 | —S—$(CH_2)_3$—(O—$CH_2$—$CH_2)_8$—CO—NHS |
| LR24 | —S—$(CH_2)_4$—(O—$CH_2$—$CH_2)_8$—CO—NHS |
| LR25 | —S—$(CH_2)_5$—(O—$CH_2$—$CH_2)_8$—CO—NHS |
| LR26 | —S—$(CH_2)_6$—(O—$CH_2$—$CH_2)_8$—CO—NHS |
| LR27 | —S—$(CH_2)_7$—(O—$CH_2$—$CH_2)_8$—CO—NHS |
| LR28 | —S—$(CH_2)_8$—(O—$CH_2$—$CH_2)_8$—CO—NHS |
| LR29 | —S—$(CH_2)_9$—(O—$CH_2$—$CH_2)_8$—CO—NHS |
| LR30 | —S—$(CH_2)_{10}$—(O—$CH_2$—$CH_2)_8$—COOH |
| LR31 | —S—$(CH_2)_2$—(O—$CH_2$—$CH_2)_9$—CO—NHS |
| LR32 | —S—$(CH_2)_2$—(O—$CH_2$—$CH_2)_{10}$—CO—NHS |
| LR33 | —S—$(CH_2)_2$—(O—$CH_2$—$CH_2)_{11}$—CO—NHS |
| LR34 | —S—$(CH_2)_2$—(O—$CH_2$—$CH_2)_{12}$—CO—NHS |
| LR35 | —S—$(CH_2)_2$—(O—$CH_2$—$CH_2)_{13}$—CO—NHS |
| LR36 | —S—$(CH_2)_2$—(O—$CH_2$—$CH_2)_{14}$—CO—NHS |
| LR37 | —S—$(CH_2)_2$—(O—$CH_2$—$CH_2)_{15}$—CO—NHS |
| LR38 | —S—$(CH_2)_2$—(O—$CH_2$—$CH_2)_{16}$—CO—NHS |
| LR39 | —S—$(CH_2)_2$—(O—$CH_2$—$CH_2)_{17}$—CO—NHS |
| LR40 | —S—$(CH_2)_2$—(O—$CH_2$—$CH_2)_{18}$—CO—NHS |
| LR41 | —S—$(CH_2)_2$—(O—$CH_2$—$CH_2)_{19}$—CO—NHS |
| LR42 | —S—$(CH_2)_2$—(O—$CH_2$—$CH_2)_{20}$—CO—NHS |
| LR43 | —S—$(CH_2)_3$—COOH |
| LR44 | —S—$(CH_2)_4$—COOH |
| LR45 | —S—$(CH_2)_5$—COOH |
| LR46 | —S—$(CH_2)_6$—COOH |
| LR47 | —S—$(CH_2)_7$—COOH |
| LR48 | —S—$(CH_2)_8$—COOH |
| LR49 | —S—$(CH_2)_9$—COOH |
| LR50 | —S—$(CH_2)_{10}$—COOH |
| LR51 | —S—$(CH_2)_3$—CO—NHS |
| LR52 | —S—$(CH_2)_4$—CO—NHS |
| LR53 | —S—$(CH_2)_5$—CO—NHS |
| LR54 | —S—$(CH_2)_6$—CO—NHS |
| LR55 | —S—$(CH_2)_7$—CO—NHS |
| LR56 | —S—$(CH_2)_8$—CO—NHS |
| LR57 | —S—$(CH_2)_9$—CO—NHS |
| LR58 | —S—$(CH_2)_{10}$—CO—NHS |

Commonly used nomenclature for a copolymer comprising a total of n monomers, x % of said monomers being monomer A and y % of said monomers being monomer B is: $P[A_x\text{-co-}B_y]_n$. When the extremities of the copolymer are specific, they may be indicated on either side of $P[A_x\text{-co-}B_y]_n$, namely under the form: $R^1$—$P[A_x\text{-co-}B_y]_n$—$R^2$. This nomenclature is used hereafter for the copolymer of the invention.

According to one embodiment, the ligand of the present invention is a copolymer of general formula (I):

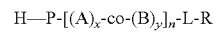

wherein

A represents an anchoring monomer having a side-chain comprising a first moiety $M_A$ having affinity for the surface of a nanocrystal;

B represents a hydrophilic monomer having a side-chain comprising a second moiety $M_B$ being hydrophilic;

n represents a positive integer, preferably an integer ranging from 1 to 1000, preferably from 1 to 499, from 1 to 249 or from 1 to 99;

x and y represent each independently a percentage of n, wherein x and y are different from 0% of n and different from 100% of n, preferably ranging from more than 0% to less than 100% of n, preferably from more than 0% to 80% of n, from more than 0% to 50% of n; wherein x+y is equal to 100% of n;

R represents:
a functional group selected from the group comprising —$NH_2$, —COOH, —OH, —SH, —CHO, ketone, halide; activated ester such as for example N-hydroxysuccinimide ester, N-hydroxyglutarimide ester or maleimide ester; activated carboxylic acid such as for example acid anhydride or acid halide; isothiocyanate; isocyanate; alkyne; azide; glutaric anhydride, succinic anhydride, maleic anhydride; hydrazide; chloroformate, maleimide, alkene, silane, hydrazone, oxime and furan; and a bioactive group selected from the group comprising avidin or streptavidin; antibody such as a monoclonal antibody or a single chain antibody; sugars; a protein or peptide sequence having a specific binding affinity for an affinity target, such as for example an avimer or an affibody (the affinity target may be for example a protein, a nucleic acid, a peptide, a metabolite or a small molecule), antigens, steroids, vitamins, drugs, haptens, metabolites, toxins, environmental pollutants, amino acids, peptides, proteins, aptamers, nucleic acids, nucleotides, peptide nucleic acid (PNA), folates, carbohydrates, lipids, phospholipid, lipoprotein, lipopolysaccharide, liposome hormone, polysaccharide, polymers, polyhistidine tags, fluorophores; and L represents a bound or a spacer selected from the group comprising alkylene, alkenylene, arylene or arylalkyl linking groups having 1 to 50 chain atoms, wherein the linking group can be optionally interrupted or terminated by —O—, —S—, —NR$_7$—, wherein R$_7$ is H or alkyl, —CO—, —NHCO—, —CONH— or a combination thereof; or a spacer selected from the group comprising DNA, RNA, peptide nucleic acid (PNA), polysaccharide, peptide.

In a preferred embodiment of the invention, R represents —COOH or —NH$_2$.

In a specific embodiment of the invention, L represents an alkylene linking group having 1 to 20 chain atoms, preferably 1 to 12 chain atoms, preferably 1, 2, 3, 4, 5, 6, 7, 8, 9, 10, 11 or 12 chain atoms, and optionally interrupted or terminated by —O— or —S—.

In one embodiment, L is of formula —S—(CH$_2$)$_{n1}$—, wherein n$_1$ is a positive integer ranging from 1 to 20, preferably 1 to 5, more preferably 1, 2 or 3.

In a specific embodiment of the invention, L represents an alkylene linking group having 3 to 20 chain atoms, preferably 3 to 12 chain atoms, preferably 3, 4, 5, 6, 7, 8, 9, 10, 11 or 12 chain atoms, and optionally interrupted or terminated by —O— or —S—.

In one embodiment, L is of formula —S—(CH$_2$)$_{n1}$—, wherein n$_1$ is a positive integer higher than 2, preferably 3 to 12 chain atoms, preferably 3, 4, 5, 6, 7, 8, 9, 10, 11 or 12 chain atoms.

In another embodiment, L represents an ethylene glycol derivative, preferably of formula —[CH$_2$—CH$_2$—O]$_{n2}$—(CH$_2$)$_{n3}$—S— wherein n$_2$ and n$_3$ are each independently positive integers and n$_2$+n$_3$ is higher than 2; preferably n$_2$+n$_3$ is ranging from 3 to 230. In one embodiment, L represents an ethylene glycol derivative, preferably of formula —[CH$_2$—CH$_2$—O]$_{n2}$—(CH$_2$)$_{n3}$—S— wherein n$_2$ and n$_3$ are each independently positive integers and n$_2$+n$_3$ is ranging from 3 to 120; preferably is 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119 and 120.

In one embodiment, L represents an ethylene glycol derivative, preferably of formula —[CH$_2$—CH$_2$—O]$_{n2}$—(CH$_2$)$_{n3}$—S— wherein n$_2$ and n$_3$ are each independently positive integers and n$_2$+n$_3$ is ranging from 3 to 50; preferably is 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 and 50.

In another embodiment, L represents an ethylene glycol derivative, preferably of formula —[CH$_2$—CH$_2$—O]$_{n2}$—(CH$_2$)$_{n3}$—S— wherein n$_2$ and n$_3$ are each independently positive integers ranging from 1 to 20, preferably 1, 2, 3, 4, 5, 6 7, 8, 9 or 10, more preferably n$_2$ is equal to 8 and n$_3$ is equal to 2.

In another embodiment, L represents a poly(ethylene glycol) derivative having a molecular weight less than 10 000 g/mol; preferably less than 5 000 g/mol; more preferably less than 1 000 g/mol.

In one embodiment, L represents a poly(ethylene glycol) derivative having a molecular weight ranging from 300 g/mol to 1 000 g/mol. In one embodiment, L represents a poly(ethylene glycol) derivative having a molecular weight ranging from 44 g/mol to 300 g/mol.

In one embodiment, L represents a poly(ethylene glycol) derivative having a molecular weight of about 400 g/mol.

In one embodiment, L represents a poly(ethylene glycol) derivative having a molecular weight of about 300 g/mol.

In another embodiment, -L-R represents —S—(CH$_2$)$_{n3}$—[CH$_2$—CH$_2$—O]$_{n2}$—COOH wherein n$_2$ and n$_3$ are each independently positive integers and n$_2$+n$_3$ is higher than 2; preferably n$_2$+n$_3$ is ranging from 3 to 230; more preferably ranging from 5 to 115: more preferably n$_2$ is equal to 8 and n$_3$ is equal to 2.

In another embodiment, -L-R does not represent —S—(CH$_2$)$_{n3}$—COOH wherein n$_3$ is ranging from 1 to 11.

In another embodiment, -L-R does not represent —S—(CH$_2$)$_{n3}$—NH$_2$ wherein n$_3$ is ranging from 2 to 11.

In one embodiment of the invention, n is ranging from 1 to 1000, from 1 to 499, from 1 to 249, from 1 to 99, from 5 to 75, from 5 to 50, from 10 to 50, from 10 to 30, from 5 to 35, from 5 to 25, from 15 to 25.

In one embodiment, x and y are each independently a percentage of n, preferably a percentage selected in the group of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50% of n.

According to an embodiment, the ligand of the present invention is a copolymer of general formula (II):

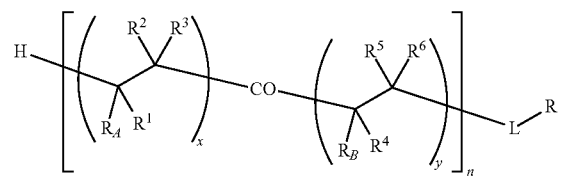

wherein n, x, y, L and R are as defined in formula (I);

R$_A$ represents a group comprising the first moiety M$_A$ having affinity for the surface of a nanocrystal;

$R_B$ represents a group comprising the second moiety $M_B$ being hydrophilic;

$R^1, R^2, R^3, R^4, R^5$ and $R^6$ represent each independently H or a group selected from the alkyl, alkenyl, aryl, hydroxyl, halogen, alkoxy and carboxylate, amide.

In one embodiment of the invention, $R^2, R^3, R^5$ and $R^6$ are H.

In one embodiment of the invention, $R^1$ and $R^4$ are alkyl groups, preferably methyl.

In one embodiment of the invention, said first moiety $M_A$ having affinity for the surface of a nanocrystal and in particular affinity for a metal present at the surface of a nanocrystal includes, but is not limited to, a thiol moiety, a dithiol moiety, an imidazole moiety, a catechol moiety, a pyridine moiety, a pyrrole moiety, a thiophene moiety, a thiazole moiety, a pyrazine moiety, a carboxylic acid or carboxylate moiety, a naphthyridine moiety, a phosphine moiety, a phosphine oxide moiety, a phenol moiety, a primary amine moiety, a secondary amine moiety, a tertiary amine moiety, a quaternary amine moiety, an aromatic amine moiety, or a combination thereof.

In one embodiment of the invention, said first moiety $M_A$ having affinity for the surface of a nanocrystal and in particular affinity for a material E selected in the group of O, S, Se, Te, N, P, As, and mixture thereof, includes, but is not limited to, an imidazole moiety, a pyridine moiety, a pyrrole moiety, a thiazole moiety, a pyrazine moiety, a naphthyridine moiety, a phosphine moiety, a phosphine oxide moiety, a primary amine moiety, a secondary amine moiety, a tertiary amine moiety, a quaternary amine moiety, an aromatic amine moiety, or a combination thereof.

In one embodiment of the invention, said first moiety $M_A$ having affinity for the surface of a nanocrystal is a dithiol moiety, preferably a propane-1,3-dithiol, more preferably a propan-1-yl-1,3-dithiol moiety.

In one embodiment of the invention, said second moiety $M_B$ being hydrophilic includes, but is not limited to, a zwitterionic moiety (i.e. any compound having both a negative charge and a positive charge, preferably a group with both an ammonium group and a sulfonate group or a group with both an ammonium group and a carboxylate group) such as for example an aminocarboxylate, an aminosulfonate, a carboxybetaine moiety wherein the ammonium group may be included in an aliphatic chain, a five-membered cycle, a five-membered heterocycle comprising 1, 2 or 3 further nitrogen atoms, a six-membered cycle, a six-membered heterocycle comprising 1, 2, 3 or 4 further nitrogen atoms, a sulfobetaine moiety wherein the ammonium group may be included in an aliphatic chain, a five-membered cycle, a five-membered heterocycle comprising 1, 2 or 3 further nitrogen atoms, a six-membered cycle, a six-membered heterocycle comprising 1, 2, 3 or 4 further nitrogen atoms, a phosphobetaine wherein the ammonium group may be included in an aliphatic chain, a five-membered cycle, a five-membered heterocycle comprising 1, 2 or 3 further nitrogen atoms, a six-membered cycle, a six-membered heterocycle comprising 1, 2, 3 or 4 further nitrogen atoms, a phosphorylcholine, a phosphocholine moiety, and combinations thereof or a PEG moiety or poly(ether)glycol moiety.

An example of a suitable poly(ether)glycol moiety is $-[O-CH_2-CHR']_n-R''$, wherein R' can be H or $C_1$-$C_3$ alkyl, R'' can be H, $-OH$, $C_1$-$C_6$ alkyl, $C_1$-$C_6$ alkoxy, aryl, aryloxy, arylalkyl, or arylalkoxy and n can be an integer in the range of 1 to 120, preferably of 1 to 60, more preferably of 1 to 30.

In another embodiment of the invention, said second moiety $M_B$ being hydrophilic is not a PEG moiety.

In one embodiment of the invention, said second moiety $M_B$ being hydrophilic is a sulfobetaine group.

According to an embodiment, the ligand of the present invention is a copolymer of general formula (III):

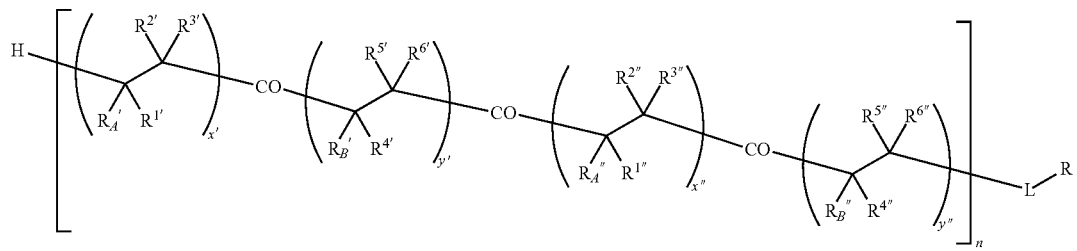

wherein

L and R are as defined in formula (I);

$R_A'$ and $R_A''$ represent respectively a group comprising a first moiety $M_A'$ and a group comprising a first moiety $M_A''$, said moieties $M_A'$ and $M_A''$ having affinity for the surface of a nanocrystal;

$R_B'$ and $R_B''$ represent respectively a group comprising a second moiety $M_B'$ and a group comprising a second moiety $M_B''$, said moieties $M_B'$ and $M_B''$ being hydrophilic;

$R^{1'}, R^{2'}, R^{3'}, R^{4'}, R^{5'}, R^{6'}, R^{1''}, R^{2''}, R^{3''}, R^{4''}, R^{5''}$ and $R^{6''}$ represent each independently H or a group selected from the alkyl, alkenyl, aryl, hydroxyl, halogen, alkoxy and carboxylate, amide;

n represents a positive integer, preferably an integer ranging from 1 to 1000, preferably from 1 to 499, from 1 to 249 or from 1 to 99;

x' and x'' represent each independently a percentage of n, wherein at least one of x' and x'' is different from 0% of n; wherein x' and x'' are different from 100% of n, preferably x' and x'' are ranging from more than 0% to less than 100% of n, preferably from more than 0% to 50% of n, from more than 0% to 50% of n;

y' and y'' represent each independently a percentage of n, wherein at least one of y' and y'' is different from 0% of n; wherein y' and y'' are different from 100% of n, preferably y' and y'' are from more than 0% to less than 100% of n, preferably from more than 0% to 50% of n, from more than 0% to 50% of n;

wherein x'+x''+y'+y'' is equal to 100% of n.

In one embodiment, each of x' and x'' is independently a percentage of n, preferably a percentage selected in the group of 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50% of n, with the condition that at least one of x' and x" is not 0%.

In one embodiment, each of y' and y" is independently a percentage of n, preferably a percentage selected in the group of 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50% of n, with the condition that at least one of y' and y" is not 0%.

In one embodiment of the invention, $R_2'$, $R_3'$, $R_2"$, $R_3"$, $R_5'$, $R_6'$, $R_5"$ and $R_6"$ are H.

In one embodiment of the invention, $R_1'$, $R_1"$, $R_4'$ and $R_4"$ are alkyl groups, preferably methyl.

In one embodiment of the invention, said moiety $M_A$ comprises said moieties $M_A'$ and $M_A"$. In one embodiment of the invention, said moiety $M_B$ comprises said moieties $M_B'$ and $M_B"$.

In one embodiment of the invention, said x is equal to x'+x". In one embodiment of the invention, said y is equal to y'+y".

In one embodiment of the invention, said first moieties $M_A'$ and $M_A"$ having affinity for the surface of a nanocrystal and in particular affinity for a metal present at the surface of a nanocrystal include, but is not limited to, a thiol moiety, a dithiol moiety, an imidazole moiety, a catechol moiety, a pyridine moiety, a pyrrole moiety, a thiophene moiety, a thiazole moiety, a pyrazine moiety, a carboxylic acid or carboxylate moiety, a naphthyridine moiety, a phosphine moiety, a phosphine oxide moiety, a phenol moiety, a primary amine moiety, a secondary amine moiety, a tertiary amine moiety, a quaternary amine moiety, an aromatic amine moiety, or a combination thereof.

In one embodiment of the invention, said first moieties $M_A'$ and $M_A"$ having affinity for the surface of a nanocrystal and in particular affinity for a material E selected in the group of O, S, Se, Te, N, P, As, and mixture thereof, include, but is not limited to, an imidazole moiety, a pyridine moiety, a pyrrole moiety, a thiazole moiety, a pyrazine moiety, a naphthyridine moiety, a phosphine moiety, a phosphine oxide moiety, a primary amine moiety, a secondary amine moiety, a tertiary amine moiety, a quaternary amine moiety, an aromatic amine moiety, or a combination thereof.

In one embodiment of the invention, said first moiety $M_A'$ having affinity for the surface of a nanocrystal is a dithiol moiety and said first moiety $M_A"$ having affinity for the surface of a nanocrystal is an imidazole moiety.

In one embodiment of the invention, said second moieties $M_B'$ and $M_B"$ being hydrophilic include, but is not limited to, a zwitterionic moiety (i.e. any compound having both a negative charge and a positive charge, preferably a group with both an ammonium group and a sulfonate group or a group with both an ammonium group and a carboxylate group) such as for example an aminocarboxylate, an aminosulfonate, a carboxybetaine moiety wherein the ammonium group may be included in an aliphatic chain, a five-membered cycle, a five-membered heterocycle comprising 1, 2 or 3 further nitrogen atoms, a six-membered cycle, a six-membered heterocycle comprising 1, 2, 3 or 4 further nitrogen atoms, a sulfobetaine moiety wherein the ammonium group may be included in an aliphatic chain, a five-membered cycle, a five-membered heterocycle comprising 1, 2 or 3 further nitrogen atoms, a six-membered cycle, a six-membered heterocycle comprising 1, 2, 3 or 4 further nitrogen atoms, a phosphobetaine wherein the ammonium group may be included in an aliphatic chain, a five-membered cycle, a five-membered heterocycle comprising 1, 2 or 3 further nitrogen atoms, a six-membered cycle, a six-membered heterocycle comprising 1, 2, 3 or 4 further nitrogen atoms, a phosphorylcholine, a phosphocholine moiety, and combinations thereof or a PEG moiety or a poly(ether)glycol moiety, wherein if $M_B'$ is a PEG moiety, then $M_B"$ is not a PEG moiety and inversely.

In one embodiment of the invention, said second moiety $M_B'$ being hydrophilic is a sulfobetaine group and said second moiety $M_B"$ being hydrophilic is a PEG moiety or a poly(ether)glycol moiety.

In one embodiment, the ligand of the invention is a copolymer synthesized from at least 2 monomers, said monomers being:

one anchoring monomer A wherein $M_A$ is a dithiol group, one hydropohilic monomer B wherein $M_B$ is a sulfobetaine group.

In one embodiment of the invention, $R_A$ comprising the first moiety $M_A$ can have the formula -$L_A$-$M_A$, wherein $L_A$ can be a bond or an alkylene, alkenylene, or arylene linking group having 1 to 50 chain atoms and can be optionally interrupted or terminated by —O—, —S—, —NR$_7$—, wherein R$_7$ is H or alkyl, —CO—, —NHCO—, —CONH— or a combination thereof and $M_A$ corresponds to the first moiety as described here above.

Preferably, $L_A$ is —C(=O)—NH—(CH$_2$)$_m$—NH—C(=O)—(CH$_2$)$_p$—, wherein m is an integer ranging from 1 to 20, preferably from 1 to 10, preferably from 1 to 5, preferably 2, 3, 4 and p is an integer ranging from 1 to 20, preferably from 1 to 10, preferably from 1 to 6, preferably 3, 4, 5.

In a preferred embodiment, -$L_A$-$M_A$ is:

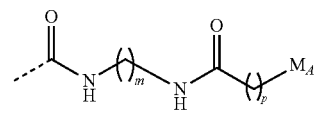

wherein m, p and $M_A$ are as defined above, preferably m is equal to 3 and p is equal to 4.

In a preferred embodiment, $M_A$ is a dithiol moiety and -$L_A$-$M_A$ may be represented by:

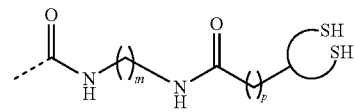

wherein m, p and $M_A$ are as defined above, preferably m is equal to 3 and p is equal to 4.

In a preferred embodiment, -$L_A$-$M_A$ is:

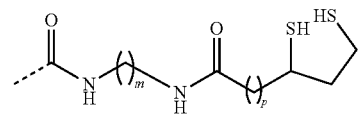

wherein m, p and $M_A$ are as defined above preferably m is equal to 3 and p is equal to 4.

In a preferred embodiment, -$L_A$-$M_A$ is:

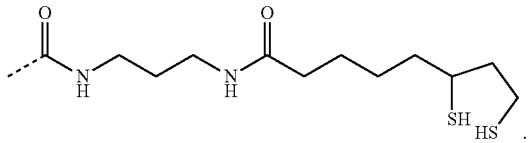

In one embodiment of the invention, $R_B$ comprising the second moiety $M_B$ can have the formula -$L_B$-$M_B$, wherein $L_B$ can be a bond or an alkylene, alkenylene, or arylene linking group having 1 to 50 chain atoms and can be optionally interrupted or terminated by —O—, —S—, —$NR_7$—, wherein $R_7$ is H or alkyl, —CO—, —NHCO—, —CONH— or a combination thereof and $M_B$ corresponds to the second moiety as described here above.

Preferably, $L_B$ is —C(=O)—NH—$(CH_2)_q$—, wherein q is an integer ranging from 1 to 20, preferably from 1 to 10, preferably from 1 to 5, preferably 2, 3, 4.

In a preferred embodiment, -$L_B$-$M_B$ is:

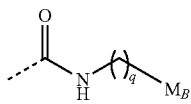

wherein q and $M_B$ are as defined above, preferably q is equal to 3.

In a preferred embodiment, -$L_B$-$M_B$ may be represented by:

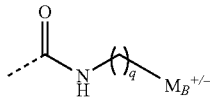

wherein q is as defined above and $M_B$ is a zwitterionic moiety, preferably q is equal to 3.

In one preferred embodiment, -$L_B$-$M_B$ may be represented by:

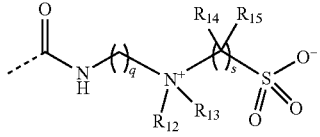

wherein q is as defined above, preferably q is equal to 3 s is an integer ranging from 1 to 5, preferably s is equal 2, 3 or 4, $R_{12}$, $R_{13}$, $R_{14}$ and $R_{15}$ are each independently H, or a group selected from an alkyl, alkenyl, aryl, hydroxyle, halogen, alkoxy, carboxylate.

In another preferred embodiment, -$L_B$-$M_B$ may be represented by:

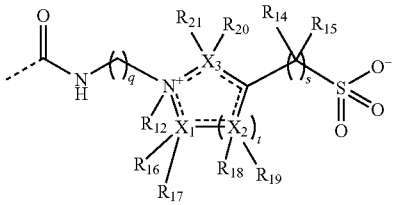

wherein q is as defined above, preferably q is equal to 3, s is an integer ranging from 1 to 5, preferably s is equal 2, 3 or 4, t is 1 or 2, $R_{14}$ and $R_{15}$ are each independently H, or a group selected from an alkyl, alkenyl, aryl, hydroxyle, halogen, alkoxy, carboxylate, $X_1$, $X_2$ and $X_3$ are each independently N or C, the bounds represented by a dotted line being each independently either absent or present, $R_{12}$, $R_{16}$, $R_{17}$, $R_{18}$, $R_{19}$, $R_{20}$ and $R_{21}$ are each independently H, or a group selected from an alkyl, alkenyl, aryl, hydroxyle, halogen, alkoxy, carboxylate, or may be absent when the bound represented by a dotted line is present.

In a preferred embodiment -$L_B$-$M_B$ is:

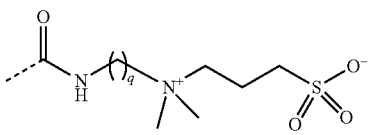

wherein q is as defined above.

In a preferred embodiment -$L_B$-$M_B$ is:

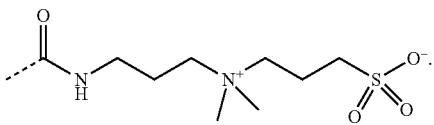

In a specific embodiment, the ligand of the invention is of formula (I-a):

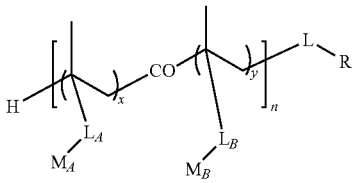

wherein n, x, y, L, R, $L_A$, $M_A$, $L_B$ and $R_B$ are as defined above.

In a specific embodiment, the ligand of the invention is of formula (I-b):

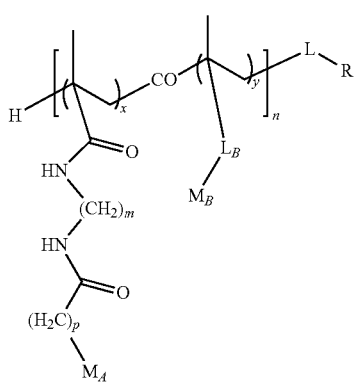

wherein n, x, y, L, R, m, p, $M_A$, $L_B$ and $M_B$ are as defined above.

In a specific embodiment, the ligand of the invention is of formula (I-c):

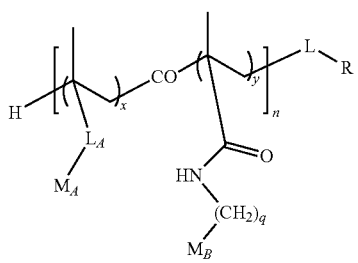

wherein n, x, y, L, R, q, $M_B$, $L_A$ and $M_A$ are as defined above.

In a specific embodiment, the ligand of the invention is of formula (I-d):

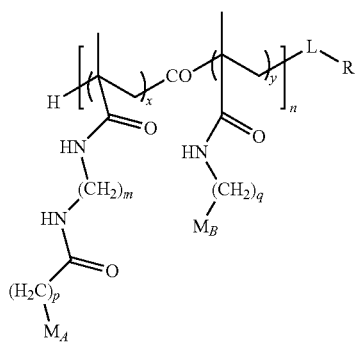

wherein n, x, y, L, R, m, p, $M_A$, q and $M_B$ are as defined above.

In a specific embodiment, the ligand of the invention is of formula (I-e):

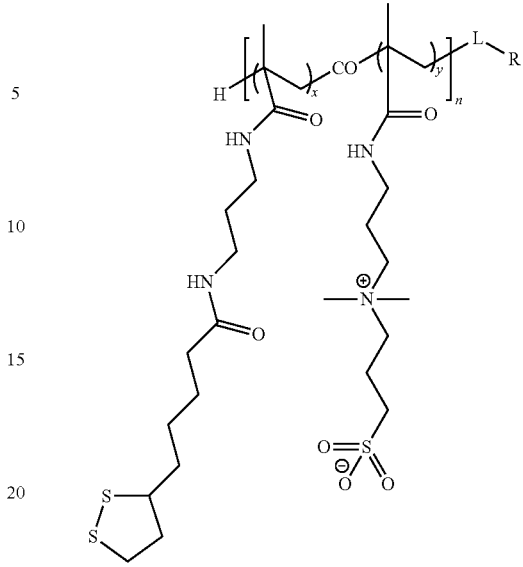

wherein n, x, y, L and R are as defined in formula (I) above; or a reduced form thereof.

In another specific embodiment, the ligand of the invention is of formula (I-f):

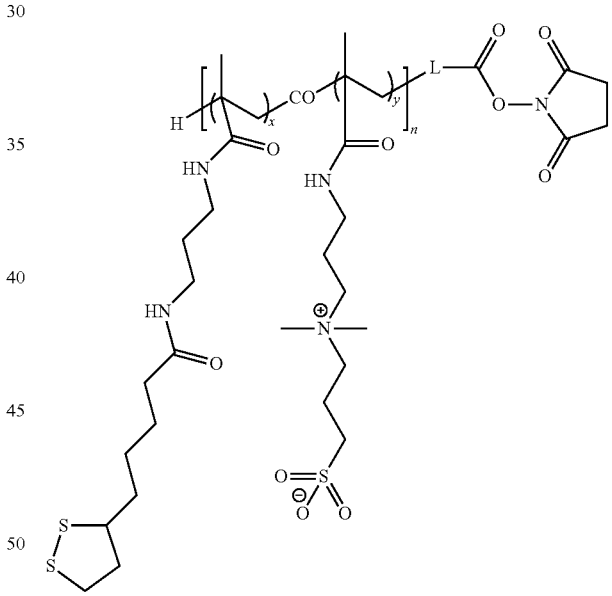

wherein n, x, y and L are as defined in formula (I) above; or a reduced form thereof.

In one embodiment of the invention, the ligand has a molecular weight from about 1,000 g/mol to about 200,000 g/mol, preferably from about 1,000 g/mol to about 100,000 g/mol, preferably from about 1,000 g/mol to about 50,000 g/mol, from about 2,000 g/mol to 50,000 g/mol, more preferably from about 2,000 g/mol to about 10,000 g/mol, from about 2,000 g/mol to 10,000 g/mol.

In one embodiment of the invention, the ligand has a polydispersity index inferior to 10, preferably inferior to 9, 8, 7, 6, 5, 4, 3, 2, 1.

In one embodiment of the invention, the ligand has a ratio of monomers A/B in number from about 1/99 to about 99/1.

In a particular embodiment, the ligand has a ratio of monomers A/B in number from about 1/99 to about 50/50, preferably from about 3/97 to about 40/60, more preferably from about 10/90 to about 50/50. In another particular embodiment, the ligand has a ratio of monomers A/B in number from about 50/50 to about 99/1, preferably from about 40/60 to about 90/10. In another embodiment, the ligand has a ratio of monomers A/B in number from about 1/99 to about 75/25, preferably from about 5/95 to about 50/50, more preferably from about 5/95 to about 25/75. In a specific embodiment, the ligand has a ratio of monomers A/B in number of about 50/50. In a specific embodiment, the ligand has a ratio of monomers A/B in number of about 20/80.

According to one embodiment, the synthesis of the ligand may be performed in presence of monomer A and monomer B with a ratio of molar amounts of A to B ranging from 1/99 to 99/1, preferably from 5/95 to 50/50, preferably from 10/90 to 50/50; preferably from 10/90 to 30/70, more preferably 20/80.

In another embodiment, of the invention, the ligand is a copolymer synthesized from at least 3 monomers, said monomers being:
one anchoring monomer A as defined above,
one hydrophilic monomer B as defined above,
one hydrophobic monomer C having a side-chain comprising a hydrophobic function $M_C$,
and wherein one end of copolymer is H and the other end comprises a functional group or a bioactive group.

According to an embodiment, the ligand of the present invention is a copolymer of general formula (IV):

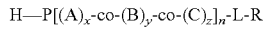

wherein
A, B, L, R and n are as defined above;
C represents an hydrophobic monomer having a side-chain comprising a moiety $M_C$ being hydrophobic;
x, y and z represent each independently a percentage of n, wherein x and y are different from 0% of n and different from 100% of n, preferably x, y and z are ranging from more than 0% to less than 100% of n, preferably from more than 0% to 80% of n, from more than 0% to 50% of n and wherein x+y+z is equal to 100% of n.

According to an embodiment, the ligand of the present invention is a copolymer of general formula (V):

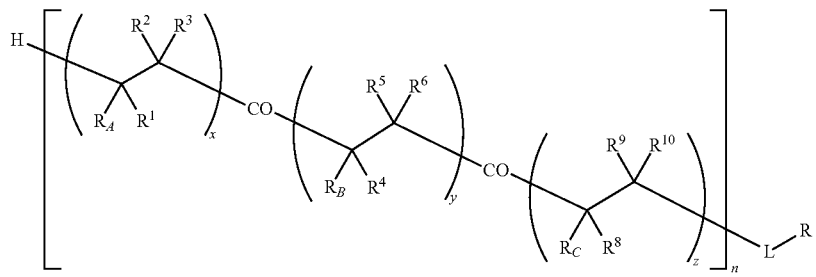

wherein
n, L, R, $R_A$, $R_B$, $R^1$, $R^2$, $R^3$, $R^4$, $R^5$ and $R^6$ are as defined above;
$R_C$ represents a group comprising the third moiety $M_C$ being hydrophobic;
$R^8$, $R^9$, and $R^{10}$ represent each independently H or a group selected from the alkyl, alkenyl, aryl, hydroxyl, halogen, alkoxy and carboxylate, amide;

x, y and z represent each independently a percentage of n, wherein x and y are different from 0% of n and different from 100% of n, preferably x, y and z are ranging from more than 0% to less than 100% of n, preferably from more than 0% to 80% of n, from more than 0% to 50% of n; and wherein x+y+z is equal to 100% of n.

In one embodiment of the invention, $R^2$, $R^3$, $R^5$, $R^6$, $R^9$, and $R^{10}$ are H.

In one embodiment, $R^1$, $R^4$, and $R^8$ are alkyl groups, preferably methyl.

According to one embodiment, said third moiety $M_C$ being hydrophobic includes, but is not limited to, alkyl, aryl, alkylaryl, arylalkyl, alkenyl groups.

According to one embodiment, preferred monomers C are those described in the following table:

| Compound n° | Name |
|---|---|
| C-1 | N-hexylmethacrylamide |
| C-2 | N-heptylmethacrylamide |
| C-3 | N-octylmethacrylamide |
| C-4 | N-nonylmethacrylamide |
| C-5 | N-decylmethacrylamide |
| C-6 | N-hexylacrylamide |
| C-7 | N-heptylacrylamide |
| C-8 | N-octylacrylamide |
| C-9 | N-nonylacrylamide |
| C-10 | N-decylacrylamide |
| C-11 | N-(2-(1H-imidazol-1-yl)ethyl)methacrylamide |
| C-12 | N-(2-(1H-imidazol-1-yl)ethyl)acrylamide |
| C-13 | N-(2-(4H-imidazol-4-yl)ethyl)methacrylamide |
| C-14 | N-(2-(4H-imidazol-4-yl)ethyl)acrylamide |
| C-15 | N-phenylmethacrylamide |
| C-16 | N-benzylmethacrylamide |
| C-17 | N-isopropylmethacrylamide |
| C-18 | N-isobutylmethacrylamide |
| C-19 | N-phenylacrylamide |
| C-20 | N-benzylacrylamide |
| C-21 | N-isopropylacrylamide |
| C-22 | N-isobutylacrylamide |
| C-23 | N-hexylmethacrylate |
| C-24 | N-heptylmethacrylate |
| C-25 | N-octylmethacrylate |
| C-26 | N-nonylmethacrylate |
| C-27 | N-decylmethacrylate |
| C-28 | N-hexylacrylate |
| C-29 | N-heptylacrylate |
| C-30 | N-octylacrylate |

-continued

| Compound n° | Name |
|---|---|
| C-31 | N-nonylacrylate |
| C-32 | N-decylacrylate |
| C-33 | N-(2-(1H-imidazol-1-yl)ethyl)methacrylate |

| Compound n° | Name |
|---|---|
| C-34 | N-(2-(1H-imidazol-1-yl)ethyl)acrylate |
| C-35 | N-(2-(4H-imidazol-4-yl)ethyl)methacrylate |
| C-36 | N-(2-(4H-imidazol-4-yl)ethyl)acrylate |
| C-37 | N-phenylmethacrylate |
| C-38 | N-benzylmethacrylate |
| C-39 | N-isopropylmethacrylate |
| C-40 | N-isobutylmethacrylate |
| C-41 | N-phenylacrylate |
| C-42 | N-benzylacrylate |
| C-43 | N-isopropylacrylate |
| C-44 | N-isobutylacrylate |

In one embodiment of the invention, $R_C$ comprising the third moiety $M_C$ can have the formula -$L_C$-$M_C$, wherein $L_C$ can be a bond or an alkylene, alkenylene or arylene linking group having 1 to 8 chain atoms.

In one embodiment of the invention, said first moiety $M_A$ is not a dihydrolipoic acid (DHLA) moiety.

In another embodiment of the invention, said first moiety $M_A$ is not an imidazole moiety.

In one embodiment, when B comprises a monomer comprising a second moiety $M_B$ which is a PEG moiety, then B further comprises at least one monomer comprising a second moiety $M_B$ which is not a PEG moiety.

In one embodiment of the invention, when the first moiety $M_A$ is an imidazole moiety, the second moiety $M_B$ is not a PEG moiety.

In one embodiment of the invention, when the first moiety $M_A$ is an imidazole moiety, the second moiety $M_B$ is not a sulfobetaine moiety. In a specific embodiment of the invention, when the first moiety $M_A$ is an imidazole moiety, the second moiety $M_B$ is not —$N^+(Me)_2$-$(CH_2)_2$—$SO_3^-$ or —$N^+(Me)_2$-$(CH_2)_3$—$SO_3^-$.

In one embodiment of the invention, when the first moiety $M_A$ is an imidazole moiety, the second moiety $M_B$ is not a carboxybetaine moiety. In a specific embodiment of the invention, when the first moiety $M_A$ is an imidazole moiety, the second moiety $M_B$ is not —$N^+(Me)_2$-$(CH_2)_2$—$COO^-$.

In one embodiment of the invention, when the first moiety $M_A$ is an imidazole moiety, the second moiety $M_B$ is not a phosphobetaine moiety. In a specific embodiment of the invention, when the first moiety $M_A$ is an imidazole moiety, the second moiety $M_B$ is not —O—$P(O_2^-)$—P—$(CH_2)_2$—$N^+(Me)_3$.

In one embodiment of the invention, when the first moiety $M_A$ is a dithiol group, and B comprises a monomer comprising a second moiety $M_B'$ which is a PEG moiety, then B further comprises at least one monomer comprising a second moiety $M_B''$ which is not a PEG moiety.

According to one embodiment, preferred combinations of monomers A and B are described in the following table:

| N° | A | B |
|---|---|---|
| 1 | 5(1,2-dithiolan-3-yl)-N-(3-methacrylamidopropyl)pentanamide | 3-((3-methacrylamidopropyl)dimethylammonio)propane-1-sulfonate |
| 2 | 6-(1,2-dithiolan-3-yl)-N-(3-methacrylamidopropyl)hexanamide | 3-((3-methacrylamidopropyl)dimethylammonio)propane-1-sulfonate |
| 3 | 7-(1,2-dithiolan-3-yl)-N-(3-methacrylamidopropyl)heptanamide | 3-((3-methacrylamidopropyl)dimethylammonio)propane-1-sulfonate |
| 4 | 8-(1,2-dithiolan-3-yl)-N-(3-methacrylamidopropyl)octanamide | 3-((3-methacrylamidopropyl)dimethylammonio)propane-1-sulfonate |
| 5 | 9-(1,2-dithiolan-3-yl)-N-(3-methacrylamidopropyl)nonanamide | 3-((3-methacrylamidopropyl)dimethylammonio)propane-1-sulfonate |
| 6 | 10-(1,2-dithiolan-3-yl)-N-(3-methacrylamidopropyl)decanamide | 3-((3-methacrylamidopropyl)dimethylammonio)propane-1-sulfonate |
| 7 | 5-(1,2-dithiolan-3-yl)-N-(3-acrylamidopropyl)pentanamide | 3-((3-methacrylamidopropyl)dimethylammonio)propane-1-sulfonate |
| 8 | 6-(1,2-dithiolan-3-yl)-N-(3-acrylamidopropyl)hexanamide | 3-((3-methacrylamidopropyl)dimethylammonio)propane-1-sulfonate |
| 9 | 7-(1,2-dithiolan-3-yl)-N-(3-acrylamidopropyl)heptanamide | 3-((3-methacrylamidopropyl)dimethylammonio)propane-1-sulfonate |
| 10 | 8-(1,2-dithiolan-3-yl)-N-(3-acrylamidopropyl)octanamide | 3-((3-methacrylamidopropyl)dimethylammonio)propane-1-sulfonate |
| 11 | 9-(1,2-dithiolan-3-yl)-N-(3-acrylamidopropyl)nonanamide | 3-((3-methacrylamidopropyl)dimethylammonio)propane-1-sulfonate |
| 12 | 10-(1,2-dithiolan-3-yl)-N-(3-acrylamidopropyl)decanamide | 3-((3-methacrylamidopropyl)dimethylammonio)propane-1-sulfonate |
| 13 | 3-(5-(1,2-dithiolan-3-yl)pentanamido)propyl methacrylate | 3-((3-methacrylamidopropyl)dimethylammonio)propane-1-sulfonate |
| 14 | 3-(6-(1,2-dithiolan-3-yl)hexanamido)propyl methacrylate | 3-((3-methacrylamidopropyl)dimethylammonio)propane-1-sulfonate |
| 15 | 3-(7-(1,2-dithiolan-3-yl)heptanamido)propyl methacrylate | 3-((3-methacrylamidopropyl)dimethylammonio)propane-1-sulfonate |
| 16 | 3-(8-(1,2-dithiolan-3-yl)octanamido)propyl methacrylate | 3-((3-methacrylamidopropyl)dimethylammonio)propane-1-sulfonate |
| 17 | 3-(9-(1,2-dithiolan-3-yl)nonanamido)propyl methacrylate | 3-((3-methacrylamidopropyl)dimethylammonio)propane-1-sulfonate |
| 18 | 3-(10-(1,2-dithiolan-3-yl)decanamido)propyl methacrylate | 3-((3-methacrylamidopropyl)dimethylammonio)propane-1-sulfonate |
| 19 | 3-(5-(1,2-dithiolan-3-yl)pentanamido)propyl acrylate | 3-((3-methacrylamidopropyl)dimethylammonio)propane-1-sulfonate |
| 20 | 3-(6-(1,2-dithiolan-3-yl)hexanamido)propyl acrylate | 3-((3-methacrylamidopropyl)dimethylammonio)propane-1-sulfonate |
| 21 | 3-(7-(1,2-dithiolan-3-ylheptamido)propyl acrylate | 3-((3-methacrylamidopropyl)dimethylammonio)propane-1-sulfonate |
| 22 | 3-(8-(1,2-dithiolan-3-yl)octanamido)propyl acrylate | 3-((3-methacrylamidopropyl)dimethylammonio)propane-1-sulfonate |
| 23 | 3-(9-(1,2-dithiolan-3-yl)nonanamido)propyl acrylate | 3-((3-methacrylamidopropyl)dimethylammonio)propane-1-sulfonate |
| 24 | 3-(10-(1,2-dithiolan-3-yl)decanamido)propyl acrylate | 3-((3-methacrylamidopropyl)dimethylammonio)propane-1-sulfonate |

| N° | A | B |
|---|---|---|
| 25 | 5-mercapto-N-(3-methacrylamido-propyl)pentanamide | 3-((3-methacrylamidopropyl)dimethylammonio)propane-1-sulfonate |
| 26 | 6-mercapto-N-(3-methacrylamido-propyl)hexanamide | 3-((3-methacrylamidopropyl)dimethylammonio)propane-1-sulfonate |
| 27 | 7-mercapto-N-(3-methacrylamido-propyl)heptanamide | 3-((3-methacrylamidopropyl)dimethylammonio)propane-1-sulfonate |
| 28 | 8-mercapto-N-(3-methacrylamido-propyl)octanamide | 3-((3-methacrylamidopropyl)dimethylammonio)propane-1-sulfonate |
| 29 | 9-mercapto-N-(3-methacrylamido-propyl)nonanamide | 3-((3-methacrylamidopropyl)dimethylammonio)propane-1-sulfonate |
| 30 | 10-mercapto-N-(3-methacrylamido-propyl)decanamide | 3-((3-methacrylamidopropyl)dimethylammonio)propane-1-sulfonate |
| 31 | N-(3-acrylamidopropyl)-5-mercaptopentanamide | 3-((3-methacrylamidopropyl)dimethylammonio)propane-1-sulfonate |
| 32 | N-(3-acryl-amidopropyl)-6-mercaptohexanamide | 3-((3-methacrylamidopropyl)dimethylammonio)propane-1-sulfonate |
| 33 | N-(3-acryl-amidopropyl)-7-mercaptoheptanamide | 3-((3-methacrylamidopropyl)dimethylammonio)propane-1-sulfonate |
| 34 | N-(3-acryl-amidopropyl)-8-mercaptooctanamide | 3-((3-methacrylamidopropyl)dimethylammonio)propane-1-sulfonate |
| 35 | N-(3-acryl-amidopropyl)-9-mercaptononanamide | 3-((3-methacrylamidopropyl)dimethylammonio)propane-1-sulfonate |
| 36 | N-(3-acryl-amidopropyl)-10-mercaptodecanamide | 3-((3-methacrylamidopropyl)dimethylammonio)propane-1-sulfonate |
| 37 | 3-(5-mercapto-pentanamido)propyl methacrylate | 3-((3-methacrylamidopropyl)dimethylammonio)propane-1-sulfonate |
| 38 | 3-(6-mercapto-hexanamido)propyl methacrylate | 3-((3-methacrylamidopropyl)dimethylammonio)propane-1-sulfonate |
| 39 | 3-(7-mercapto-heptanamido)propyl methacrylate | 3-((3-methacrylamidopropyl)dimethylammonio)propane-1-sulfonate |
| 40 | 3-(8-mercapto-octanamido)propyl methacrylate | 3-((3-methacrylamidopropyl)dimethylammonio)propane-1-sulfonate |
| 41 | 3-(9-mercapto-nonanamido)propyl methacrylate | 3-((3-methacrylamidopropyl)dimethylammonio)propane-1-sulfonate |
| 42 | 3-(10-mercapto-decanamido)propyl methacrylate | 3-((3-methacrylamidopropyl)dimethylammonio)propane-1-sulfonate |
| 43 | 3-(5-mercapto-pentanamido)propyl acrylate | 3-((3-methacrylamidopropyl)dimethylammonio)propane-1-sulfonate |
| 44 | 3-(6-mercapto-hexanamido)propyl acrylate | 3-((3-methacrylamidopropyl)dimethylammonio)propane-1-sulfonate |
| 45 | 3-(7-mercapto-heptanamido)propyl acrylate | 3-((3-methacrylamidopropyl)dimethylammonio)propane-1-sulfonate |
| 46 | 3-(8-mercapto-octanamido)propyl acrylate | 3-((3-methacrylamidopropyl)dimethylammonio)propane-1-sulfonate |
| 47 | 3-(9-mercapto-nonanamido)propyl acrylate | 3-((3-methacrylamidopropyl)dimethylammonio)propane-1-sulfonate |
| 48 | 3-(10-mercapto-decanamido)propyl acrylate | 3-((3-methacrylamidopropyl)dimethylammonio)propane-1-sulfonate |
| 49 | 5-((3-methacryl-amidopropyl)amino)-5-oxopentanoic acid | 3-((3-methacrylamidopropyl)dimethylammonio)propane-1-sulfonate |
| 50 | 6-((3-methacrylamidopropyl)amino)-6-oxohexanoic acid | 3-((3-methacrylamidopropyl)dimethylammonio)propane-1-sulfonate |
| 51 | 7-((3-methacrylamidopropyl)amino)-7-oxoheptanoic acid | 3-((3-methacrylamidopropyl)dimethylammonio)propane-1-sulfonate |
| 52 | 8-((3-methacrylamidopropyl)amino)-8-oxooctanoic acid | 3-((3-methacrylamidopropyl)dimethylammonio)propane-1-sulfonate |
| 53 | 9-((3-methacrylamidopropyl)amino)-9-oxononanoic acid | 3-((3-methacrylamidopropyl)dimethylammonio)propane-1-sulfonate |
| 54 | 10-((3-methacrylamidopropyl)amino)-10-oxodecanoic acid | 3-((3-methacrylamidopropyl)dimethylammonio)propane-1-sulfonate |
| 55 | 5-((3-acrylamidopropyl)amino)-5-oxopentanoic acid | 3-((3-methacrylamidopropyl)dimethylammonio)propane-1-sulfonate |
| 56 | 6-((3-acrylamidopropyl)amino)-6-oxohexanoic acid | 3-((3-methacrylamidopropyl)dimethylammonio)propane-1-sulfonate |
| 57 | 7-((3-acrylamidopropyl)amino)-7-oxoheptanoic acid | 3-((3-methacrylamidopropyl)dimethylammonio)propane-1-sulfonate |
| 58 | 8-((3-acrylamidopropyl)amino)-8-oxooctanoic acid | 3-((3-methacrylamidopropyl)dimethylammonio)propane-1-sulfonate |
| 59 | 9-((3-acrylamidopropyl)amino)-9-oxononanoic acid | 3-((3-methacrylamidopropyl)dimethylammonio)propane-1-sulfonate |
| 60 | 10-((3-acrylamidopropyl)amino)-10-oxodecanoic acid | 3-((3-methacrylamidopropyl)dimethylammonio)propane-1-sulfonate |
| 61 | 5-((3-(methacryloyloxy)propyl)amino)-5-oxopentanoic acid | 3-((3-methacrylamidopropyl)dimethylammonio)propane-1-sulfonate |
| 62 | 6-((3-(methacryloyloxy)propyl)amino)-6-oxohexanoic acid | 3-((3-methacrylamidopropyl)dimethylammonio)propane-1-sulfonate |
| 63 | 7-((3-(methacryloyloxy)propyl)amino)-7-oxoheptanoic acid | 3-((3-methacrylamidopropyl)dimethylammonio)propane-1-sulfonate |
| 64 | 8-((3-(methacryloyloxy)propyl)amino)-8-oxooctanoic acid | 3-((3-methacrylamidopropyl)dimethylammonio)propane-1-sulfonate |
| 65 | 9-((3-(methacryloyloxy)propyl)amino)-9-oxononanoic acid | 3-((3-methacrylamidopropyl)dimethylammonio)propane-1-sulfonate |
| 66 | 10-((3-(methacryloyloxy)propyl)amino)-10-oxodecanoic acid | 3-((3-methacrylamidopropyl)dimethylammonio)propane-1-sulfonate |
| 67 | 5-((3-(acryloyloxy)propyl)amino)-5-oxopentanoic acid | 3-((3-methacrylamidopropyl)dimethylammonio)propane-1-sulfonate |
| 68 | 6-((3-(acryloyloxy)propyl)amino)-6-oxohexanoic acid | 3-((3-methacrylamidopropyl)dimethylammonio)propane-1-sulfonate |
| 69 | 7-((3-(acryloyloxy)propyl)amino)-7-oxoheptanoic acid | 3-((3-methacrylamidopropyl)dimethylammonio)propane-1-sulfonate |
| 70 | 8-((3-(acryloyloxy)propyl)amino)-8-oxooctanoic acid | 3-((3-methacrylamidopropyl)dimethylammonio)propane-1-sulfonate |
| 71 | 9-((3-(acryloyloxy)propyl)amino)-9-oxononanoic acid | 3-((3-methacrylamidopropyl)dimethylammonio)propane-1-sulfonate |

-continued

| N° | A | B |
|---|---|---|
| 72 | 10-((3-(acryloyloxy)propyl)amino)-10-oxodecanoic acid | 3-((3-methacrylamidopropyl)dimethylammonio)propane-1-sulfonate |
| 73 | 5-amino-N-(3-methacrylamidopropyl)pentanamide | 3-((3-methacrylamidopropyl)dimethylammonio)propane-1-sulfonate |
| 74 | 6-amino-N-(3-methacrylamidopropyl)hexanamide | 3-((3-methacrylamidopropyl)dimethylammonio)propane-1-sulfonate |
| 75 | 7-amino-N-(3-methacrylamidopropyl)heptanamide | 3-((3-methacrylamidopropyl)dimethylammonio)propane-1-sulfonate |
| 76 | 8-amino-N-(3-methacrylamidopropyl)octanamide | 3-((3-methacrylamidopropyl)dimethylammonio)propane-1-sulfonate |
| 77 | 9-amino-N-(3-methacrylamidopropyl)nonanamide | 3-((3-methacrylamidopropyl)dimethylammonio)propane-1-sulfonate |
| 78 | 10-amino-N-(3-methacrylamidopropyl)decanamide | 3-((3-methacrylamidopropyl)dimethylammonio)propane-1-sulfonate |
| 79 | N-(3-acrylamidopropyl)-5-aminopentanamide | 3-((3-methacrylamidopropyl)dimethylammonio)propane-1-sulfonate |
| 80 | N-(3-acrylamidopropyl)-6-aminohexanamide | 3-((3-methacrylamidopropyl)dimethylammonio)propane-1-sulfonate |
| 81 | N-(3-acrylamidopropyl)-7-aminheptanamide | 3-((3-methacrylamidopropyl)dimethylammonio)propane-1-sulfonate |
| 82 | N-(3-acrylamidopropyl)-8-aminooctanamide | 3-((3-methacrylamidopropyl)dimethylammonio)propane-1-sulfonate |
| 83 | N-(3-acrylamidopropyl)-9-aminononanamide | 3-((3-methacrylamidopropyl)dimethylammonio)propane-1-sulfonate |
| 84 | N-(3-acrylamidopropyl)-10-aminodecanamide | 3-((3-methacrylamidopropyl)dimethylammonio)propane-1-sulfonate |
| 85 | 3-(5-aminopentanamido)propyl methacrylate | 3-((3-methacrylamidopropyl)dimethylammonio)propane-1-sulfonate |
| 86 | 3-(6-aminohexanamido)propyl methacrylate | 3-((3-methacrylamidopropyl)dimethylammonio)propane-1-sulfonate |
| 87 | 3-(7-aminoheptanamido)propyl methacrylate | 3-((3-methacrylamidopropyl)dimethylammonio)propane-1-sulfonate |
| 88 | 3-(8-aminooctanamido)propyl methacrylate | 3-((3-methacrylamidopropyl)dimethylammonio)propane-1-sulfonate |
| 89 | 3-(9-aminononamido)propyl methacrylate | 3-((3-methacrylamidopropyl)dimethylammonio)propane-1-sulfonate |
| 90 | 3-(10-aminodecanamido)propyl methacrylate | 3-((3-methacrylamidopropyl)dimethylammonio)propane-1-sulfonate |
| 91 | 3-(5-aminopentanamido)propyl acrylate | 3-((3-methacrylamidopropyl)dimethylammonio)propane-1-sulfonate |
| 92 | 3-(6-aminohexanamido)propyl acrylate | 3-((3-methacrylamidopropyl)dimethylammonio)propane-1-sulfonate |
| 93 | 3-(7-aminoheptanamido)propyl acrylate | 3-((3-methacrylamidopropyl)dimethylammonio)propane-1-sulfonate |
| 94 | 3-(8-aminooctanamido)propyl acrylate | 3-((3-methacrylamidopropyl)dimethylammonio)propane-1-sulfonate |
| 95 | 3-(9-aminononamido)propyl acrylate | 3-((3-methacrylamidopropyl)dimethylammonio)propane-1-sulfonate |
| 96 | 3-(10-aminodecanamido)propyl acrylate | 3-((3-methacrylamidopropyl)dimethylammonio)propane-1-sulfonate |
| 97 | 5-(1H-imidazol-1-yl)-N-(3-methacrylamidopropyl)pentanamide | 3-((3-methacrylamidopropyl)dimethylammonio)propane-1-sulfonate |
| 98 | 6-(1H-imidazol-1-yl)-N-(3-methacrylamidopropyl)hexanamide | 3-((3-methacrylamidopropyl)dimethylammonio)propane-1-sulfonate |
| 99 | 7-(1H-imidazol-1-yl)-N-(3-methacrylamidopropyl)heptanamide | 3-((3-methacrylamidopropyl)dimethylammonio)propane-1-sulfonate |
| 100 | 8-(1H-imidazol-1-yl)-N-(3-methacrylamidopropyl)octanamide | 3-((3-methacrylamidopropyl)dimethylammonio)propane-1-sulfonate |
| 101 | 9-(1H-imidazol-1-yl)-N-(3-methacrylamidopropyl)nonanamide | 3-((3-methacrylamidopropyl)dimethylammonio)propane-1-sulfonate |
| 102 | 10-(1H-imidazol-1-yl)-N-(3-methacrylamidopropyl)decanamide | 3-((3-methacrylamidopropyl)dimethylammonio)propane-1-sulfonate |
| 103 | N-(3-acrylamidopropyl)-5-(1H-imidazol-1-yl)pentanamide | 3-((3-methacrylamidopropyl)dimethylammonio)propane-1-sulfonate |
| 104 | N-(3-acrylamidopropyl)-6-(1H-imidazol-1-yl)hexanamide | 3-((3-methacrylamidopropyl)dimethylammonio)propane-1-sulfonate |
| 105 | N-(3-acrylamidopropyl)-7-(1H-imidazol-1-yl)hepanamide | 3-((3-methacrylamidopropyl)dimethylammonio)propane-1-sulfonate |
| 106 | N-(3-acrylamidopropyl)-8-(1H-imidazol-1-yl)octanamide | 3-((3-methacrylamidopropyl)dimethylammonio)propane-1-sulfonate |
| 107 | N-(3-acrylamidopropyl)-9-(1H-imidazol-1-yl)nonanamide | 3-((3-methacrylamidopropyl)dimethylammonio)propane-1-sulfonate |
| 108 | N-(3-acrylamidopropyl)-10-(1H-imidazol-1-yl)decanamide | 3-((3-methacrylamidopropyl)dimethylammonio)propane-1-sulfonate |
| 109 | 3-(5-(1H-imidazol-1-yl)pentanamido)propyl methacrylate | 3-((3-methacrylamidopropyl)dimethylammonio)propane-1-sulfonate |
| 110 | 3-(6-(1H-imidazol-1-yl)hexanamido)propyl methacrylate | 3-((3-methacrylamidopropyl)dimethylammonio)propane-1-sulfonate |
| 111 | 3-(7-(1H-imidazol-1-yl)heptanamido)propyl methacrylate | 3-((3-methacrylamidopropyl)dimethylammonio)propane-1-sulfonate |
| 112 | 3-(8-(1H-imidazol-1-yl)octanamido)propyl methacrylate | 3-((3-methacrylamidopropyl)dimethylammonio)propane-1-sulfonate |
| 113 | 3-(9-(1H-imidazol-1-yl)nonanamido)propyl methacrylate | 3-((3-methacrylamidopropyl)dimethylammonio)propane-1-sulfonate |
| 114 | 3-(10-(1H-imidazol-1-yl)decanamido)propyl methacrylate | 3-((3-methacrylamidopropyl)dimethylammonio)propane-1-sulfonate |
| 115 | 3-(5-(1H-imidazol-1-yl)pentanamido)propyl acrylate | 3-((3-methacrylamidopropyl)dimethylammonio)propane-1-sulfonate |
| 116 | 3-(6-(1H-imidazol-1-yl)hexanamido)propyl acrylate | 3-((3-methacrylamidopropyl)dimethylammonio)propane-1-sulfonate |
| 117 | 3-(7-(1H-imidazol-1-yl)heptanamido)propyl acrylate | 3-((3-methacrylamidopropyl)dimethylammonio)propane-1-sulfonate |
| 118 | 3-(8-(1H-imidazol-1-yl)octanamido)propyl acrylate | 3-((3-methacrylamidopropyl)dimethylammonio)propane-1-sulfonate |
| 119 | 3-(9-(1H-imidazol-1-yl)nonanamido)propyl acrylate | 3-((3-methacrylamidopropyl)dimethylammonio)propane-1-sulfonate |

| N° | A | B |
|---|---|---|
| 120 | 3-(10-(1H-imidazol-1-yl)decanamido)propyl acrylate | 3-((3-methacrylamidopropyl)dimethylammonio)propane-1-sulfonate |
| 121 | 5-(1,2-dithiolan-3-yl)-N-(3-methacrylamidopropyl)pentanamide | 4-((3-methacrylamidopropyl)dimethylammonio)butanoate |
| 122 | 6-(1,2-dithiolan-3-yl)-N-(3-methacrylamidopropyl)hexanamide | 4-((3-methacrylamidopropyl)dimethylammonio)butanoate |
| 123 | 7-(1,2-dithiolan-3-yl)-N-(3-methacrylamidopropyl)heptanamide | 4-((3-methacrylamidopropyl)dimethylammonio)butanoate |
| 124 | 8-(1,2-dithiolan-3-yl)-N-(3-methacrylamidopropyl)octanamide | 4-((3-methacrylamidopropyl)dimethylammonio)butanoate |
| 125 | 9-(1,2-dithiolan-3-yl)-N-(3-methacrylamidopropyl)nonanamide | 4-((3-methacrylamidopropyl)dimethylammonio)butanoate |
| 126 | 10-(1,2-dithiolan-3-yl)-N-(3-methacrylamidopropyl)decanamide | 4-((3-methacrylamidopropyl)dimethylammonio)butanoate |
| 127 | 5-(1,2-dithiolan-3-yl)-N-(3-acrylamidopropyl)pentanamide | 4-((3-methacrylamidopropyl)dimethylammonio)butanoate |
| 128 | 6-(1,2-dithiolan-3-yl)-N-(3-acrylamidopropyl)hexanamide | 4-((3-methacrylamidopropyl)dimethylammonio)butanoate |
| 129 | 7-(1,2-dithiolan-3-yl)-N-(3-acrylamidopropyl)heptanamide | 4-((3-methacrylamidopropyl)dimethylammonio)butanoate |
| 130 | 8-(1,2-dithiolan-3-yl)-N-(3-acrylamidopropyl)octanamide | 4-((3-methacrylamidopropyl)dimethylammonio)butanoate |
| 131 | 9-(1,2-dithiolan-3-yl)-N-(3-acrylamidopropyl)nonanamide | 4-((3-methacrylamidopropyl)dimethylammonio)butanoate |
| 132 | 10-(1,2-dithiolan-3-yl)-N-(3-acrylamidopropyl)decanamide | 4-((3-methacrylamidopropyl)dimethylammonio)butanoate |
| 133 | 3-(5-(1,2-dithiolan-3-yl)pentanamido)propyl methacrylate | 4-((3-methacrylamidopropyl)dimethylammonio)butanoate |
| 134 | 3-(5-(1,2-dithiolan-3-yl)hexanamido)propyl methacrylate | 4-((3-methacrylamidopropyl)dimethylammonio)butanoate |
| 135 | 3-(5-(1,2-dithiolan-3-yl)heptanamido)propyl methacrylate | 4-((3-methacrylamidopropyl)dimethylammonio)butanoate |
| 136 | 3-(5-(1,2-dithiolan-3-yl)octanamido)propyl methacrylate | 4-((3-methacrylamidopropyl)dimethylammonio)butanoate |
| 137 | 3-(5-(1,2-dithiolan-3-yl)nonanamido)propyl methacrylate | 4-((3-methacrylamidopropyl)dimethylammonio)butanoate |
| 138 | 3-(5-(1,2-dithiolan-3-yl)decanamido)propyl methacrylate | 4-((3-methacrylamidopropyl)dimethylammonio)butanoate |
| 139 | 3-(5-(1,2-dithiolan-3-yl)pentanamido)propyl acrylate | 4-((3-methacrylamidopropyl)dimethylammonio)butanoate |
| 140 | 3-(5-(1,2-dithiolan-3-yl)hexanamido)propyl acrylate | 4-((3-methacrylamidopropyl)dimethylammonio)butanoate |
| 141 | 3-(5-(1,2-dithiolan-3-yl)heptamido)propyl acrylate | 4-((3-methacrylamidopropyl)dimethylammonio)butanoate |
| 142 | 3-(5-(1,2-dithiolan-3-yl)octanamido)propyl acrylate | 4-((3-methacrylamidopropyl)dimethylammonio)butanoate |
| 143 | 3-(5-(1,2-dithiolan-3-yl)nonanamido)propyl acrylate | 4-((3-methacrylamidopropyl)dimethylammonio)butanoate |
| 144 | 3-(5-(1,2-dithiolan-3-yl)decanamido)propyl acrylate | 4-((3-methacrylamidopropyl)dimethylammonio)butanoate |
| 145 | 5-mercapto-N-(3-methacrylamidopropyl)pentanamide | 4-((3-methacrylamidopropyl)dimethylammonio)butanoate |
| 146 | 6-mercapto-N-(3-methacrylamidopropyl)hexanamide | 4-((3-methacrylamidopropyl)dimethylammonio)butanoate |
| 147 | 7-mercapto-N-(3-methacrylamidopropyl)heptanamide | 4-((3-methacrylamidopropyl)dimethylammonio)butanoate |
| 148 | 8-mercapto-N-(3-methacrylamidopropyl)octanamide | 4-((3-methacrylamidopropyl)dimethylammonio)butanoate |
| 149 | 9-mercapto-N-(3-methacrylamidopropyl)nonanamide | 4-((3-methacrylamidopropyl)dimethylammonio)butanoate |
| 150 | 10-mercapto-N-(3-methacrylamidopropyl)decanamide | 4-((3-methacrylamidopropyl)dimethylammonio)butanoate |
| 151 | N-(3-acryl-amidopropyl)-5-mercapto-pentanamide | 4-((3-methacrylamidopropyl)dimethylammonio)butanoate |
| 152 | N-(3-acryl-amidopropyl)-6-mercapto-hexanamide | 4-((3-methacrylamidopropyl)dimethylammonio)butanoate |
| 153 | N-(3-acryl-amidopropyl)-7-mercapto-heptanamide | 4-((3-methacrylamidopropyl)dimethylammonio)butanoate |
| 154 | N-(3-acryl amidopropyl)-8-mercapto-octanamide | 4-((3-methacrylamidopropyl)dimethylammonio)butanoate |
| 155 | N-(3-acryl-amidopropyl)-9-mercapto-nonanamide | 4-((3-methacrylamidopropyl)dimethylammonio)butanoate |
| 156 | N-(3-acrylamidopropyl)-10-mercaptodecanamide | 4-((3-methacrylamidopropyl)dimethylammonio)butanoate |
| 157 | 3-(5-mercapto-pentanamido)propyl methacrylate | 4-((3-methacrylamidopropyl)dimethylammonio)butanoate |
| 158 | 3-(6-mercapto hexanamido)propyl methacrylate | 4-((3-methacrylamidopropyl)dimethylammonio)butanoate |
| 159 | 3-(7-mercapto-heptanamido)propyl methacrylate | 4-((3-methacrylamidopropyl)dimethylammonio)butanoate |
| 160 | 3-(8-mercapto-octanamido)propyl methacrylate | 4-((3-methacrylamidopropyl)dimethylammonio)butanoate |
| 161 | 3-(9-mercapto-nonanamido)propyl methacrylate | 4-((3-methacrylamidopropyl)dimethylammonio)butanoate |
| 162 | 3-(10-mercapto-decanamido)propyl methacrylate | 4-((3-methacrylamidopropyl)dimethylammonio)butanoate |
| 163 | 3-(5-mercapto-pentanamido)propyl acrylate | 4-((3-methacrylamidopropyl)dimethylammonio)butanoate |
| 164 | 3-(6-mercapto-hexanamido)propyl acrylate | 4-((3-methacrylamidopropyl)dimethylammonio)butanoate |
| 165 | 3-(7-mercapto-heptanamido)propyl acrylate | 4-((3-methacrylamidopropyl)dimethylammonio)butanoate |
| 166 | 3-(8-mercapto-octanamido)propyl acrylate | 4-((3-methacrylamidopropyl)dimethylammonio)butanoate |
| 167 | 3-(9-mercapto-nonanamido)propyl acrylate | 4-((3-methacrylamidopropyl)dimethylammonio)butanoate |
| 168 | 3-(10-mercapto-decanamido)propyl acrylate | 4-((3-methacrylamidopropyl)dimethylammonio)butanoate |

| N° | A | B |
|---|---|---|
| 169 | 5-((3-methacryl-amidopropyl)amino)-5-oxopentanoic acid | 4-((3-methacrylamidopropyl)dimethylammonio)butanoate |
| 170 | 6-((3-methacryl-amidopropyl)amino)-6-oxohexanoic acid | 4-((3-methacrylamidopropyl)dimethylammonio)butanoate |
| 171 | 7-((3-methacryl-amidopropyl)amino)-7-oxoheptanoic acid | 4-((3-methacrylamidopropyl)dimethylammonio)butanoate |
| 172 | 8-((3-methacryl-amidopropyl)amino)-8-oxooctanoic acid | 4-((3-methacrylamidopropyl)dimethylammonio)butanoate |
| 173 | 9-((3-methacryl-amidopropyl)amino)-9-oxononanoic acid | 4-((3-methacrylamidopropyl)dimethylammonio)butanoate |
| 174 | 10-((3-methacryl-amidopropyl)amino)-10-oxodecanoic acid | 4-((3-methacrylamidopropyl)dimethylammonio)butanoate |
| 175 | 5-((3-acrylamido-propyl)amino)-5-oxopentanoic acid | 4-((3-methacrylamidopropyl)dimethylammonio)butanoate |
| 176 | 6-((3-acrylamido-propyl)amino)-6-oxohexanoic acid | 4-((3-methacrylamidopropyl)dimethylammonio)butanoate |
| 177 | 7-((3-acrylamido-propyl)amino)-7-oxoheptanoic acid | 4-((3-methacrylamidopropyl)dimethylammonio)butanoate |
| 178 | 8-((3-acrylamido-propyl)amino)-8-oxooctanoic acid | 4-((3-methacrylamidopropyl)dimethylammonio)butanoate |
| 179 | 9-((3-acrylamido-propyl)amino)-9-oxononanoic acid | 4-((3-methacrylamidopropyl)dimethylammonio)butanoate |
| 180 | 10-((3-acrylamido-propyl)amino)-10-oxodecanoic acid | 4-((3-methacrylamidopropyl)dimethylammonio)butanoate |
| 181 | 5-((3-(metha-cryloyloxy)propyl)amino)-5-oxopentanoic acid | 4-((3-methacrylamidopropyl)dimethylammonio)butanoate |
| 182 | 6-((3-(metha-cryloyloxy)propyl)amino)-6-oxohexanoic acid | 4-((3-methacrylamidopropyl)dimethylammonio)butanoate |
| 183 | 7-((3-(metha-cryloyloxy)propyl)amino)-7-oxoheptanoic acid | 4-((3-methacrylamidopropyl)dimethylammonio)butanoate |
| 184 | 8-((3-(metha-cryloyloxy)propyl)amino)-8-oxooctanoic acid | 4-((3-methacrylamidopropyl)dimethylammonio)butanoate |
| 185 | 9-((3-(metha-cryloyloxy)propyl)amino)-9-oxononanoic acid | 4-((3-methacrylamidopropyl)dimethylammonio)butanoate |
| 186 | 10-((3-(metha-cryloyloxy)propyl)amino)-10-oxodecanoic acid | 4-((3-methacrylamidopropyl)dimethylammonio)butanoate |
| 187 | 5-((3-(acryloyloxy)propyl)amino)-5-oxopentanoic acid | 4-((3-methacrylamidopropyl)dimethylammonio)butanoate |
| 188 | 6-((3-(acryloyloxy)propyl)amino)-6-oxohexanoic acid | 4-((3-methacrylamidopropyl)dimethylammonio)butanoate |
| 189 | 7-((3-(acryloyloxy)propyl)amino)-7-oxoheptanoic acid | 4-((3-methacrylamidopropyl)dimethylammonio)butanoate |
| 190 | 8-((3-(acryloyloxy)propyl)amino)-8-oxooctanoic acid | 4-((3-methacrylamidopropyl)dimethylammonio)butanoate |
| 191 | 9-((3-(acryloyloxy)propyl)amino)-9-oxononanoic acid | 4-((3-methacrylamidopropyl)dimethylammonio)butanoate |
| 192 | 10-((3-(acryloyloxy)propyl)amino)-10-oxodecanoic acid | 4-((3-methacrylamidopropyl)dimethylammonio)butanoate |
| 193 | 5-amino-N-(3-methacrylamido-propyl)pentanamide | 4-((3-methacrylamidopropyl)dimethylammonio)butanoate |
| 194 | 6-amino-N-(3-methacrylamido-propyl)hexanamide | 4-((3-methacrylamidopropyl)dimethylammonio)butanoate |
| 195 | 7-amino-N-(3-methacrylamido-propyl)heptanamide | 4-((3-methacrylamidopropyl)dimethylammonio)butanoate |
| 196 | 8-amino-N-(3-methacrylamido-propyl)octanamide | 4-((3-methacrylamidopropyl)dimethylammonio)butanoate |
| 197 | 9-amino-N-(3-methacrylamido-propyl)nonanamide | 4-((3-methacrylamidopropyl)dimethylammonio)butanoate |
| 198 | 10-amino-N-(3-methacrylamido-propyl)decanamide | 4-((3-methacrylamidopropyl)dimethylammonio)butanoate |
| 199 | N-(3-acrylamidopropyl)-5-aminopentanamide | 4-((3-methacrylamidopropyl)dimethylammonio)butanoate |
| 200 | N-(3-acrylamidopropyl)-6-aminohexanamide | 4-((3-methacrylamidopropyl)dimethylammonio)butanoate |
| 201 | N-(3-acrylamidopropyl)-7-aminoheptanamide | 4-((3-methacrylamidopropyl)dimethylammonio)butanoate |
| 202 | N-(3-acrylamidopropyl)-8-aminooctanamide | 4-((3-methacrylamidopropyl)dimethylammonio)butanoate |
| 203 | N-(3-acrylamidopropyl)-9-aminononanamide | 4-((3-methacrylamidopropyl)dimethylammonio)butanoate |
| 204 | N-(3-acrylamido-propyl)-10-aminodecanamide | 4-((3-methacrylamidopropyl)dimethylammonio)butanoate |
| 205 | 3-(5-aminopenta-namido)propyl methacrylate | 4-((3-methacrylamidopropyl)dimethylammonio)butanoate |
| 206 | 3-(6-aminohexa-namido)propyl methacrylate | 4-((3-methacrylamidopropyl)dimethylammonio)butanoate |
| 207 | 3-(7-aminohepta-namido)propyl methacrylate | 4-((3-methacrylamidopropyl)dimethylammonio)butanoate |
| 208 | 3-(8-aminoocta-namido)propyl methacrylate | 4-((3-methacrylamidopropyl)dimethylammonio)butanoate |
| 209 | 3-(9-amino-nonanamido)propyl methacrylate | 4-((3-methacrylamidopropyl)dimethylammonio)butanoate |
| 210 | 3-(10-aminodeca-namido)propyl methacrylate | 4-((3-methacrylamidopropyl)dimethylammonio)butanoate |
| 211 | 3-(5-aminopenta-namido)propyl acrylate | 4-((3-methacrylamidopropyl)dimethylammonio)butanoate |
| 212 | 3-(6-aminohexa-namido)propyl acrylate | 4-((3-methacrylamidopropyl)dimethylammonio)butanoate |
| 213 | 3-(7-aminohepta-namido)propyl acrylate | 4-((3-methacrylamidopropyl)dimethylammonio)butanoate |

-continued

| N° | A | B |
|---|---|---|
| 214 | 3-(8-aminoocta-namido)propyl acrylate | 4-((3-methacrylamidopropyl)dimethylammonio)butanoate |
| 215 | 3-(9-amino-nonamido)propyl acrylate | 4-((3-methacrylamidopropyl)dimethylammonio)butanoate |
| 216 | 3-(10-amino-decanamido)propyl acrylate | 4-((3-methacrylamidopropyl)dimethylammonio)butanoate |

According to one embodiment, preferred ligands comprise combinations of monomers A and B as described in the table above and -L-R is $-S-(CH_2)_2-(O-CH_2-CH_2)_8-COOH$, $-S-(CH_2)_{12}-COOH$ or any -L-R described hereabove.

The present invention further relates to a method of manufacturing of the ligand of the invention.

In one embodiment, the manufacturing process of the ligand of the invention comprises polymerizing an anchoring monomer A and a hydrophilic monomer B in presence of an initiator and a chain transfer agent (CTA).

According to one embodiment, the synthesis of the ligand may be performed by any radical polymerization known by those skilled in the art. According to one embodiment, the synthesis of the ligand may be performed by controlled radical polymerization such as RAFT polymerization (Reversible Addition-Fragmentation chain Transfer), ATRP (Atom Transfer Radical Polymerization), NMP (Nitroxide Mediated Polymerization) or iodine transfer polymerization. According to another embodiment, the synthesis of the ligand may be performed by non-controlled radical polymerization.

According to one embodiment, the synthesis of the ligand may be performed in presence of a monomer A and monomer B and a solvent such as for example acetic acid, THF, water or a mixture thereof.

In a preferred embodiment, the solvent is acetic acid.

In one embodiment, the polymerization is performed at a temperature ranging from 40° C. to 100° C., preferably from 50° C. to 70° C., more preferably at about 60° C.

In an embodiment, the polymerization is performed for a period of time ranging from 0.5 to 24 hours, preferably from 12 to 18 hours.

In one embodiment, the polymerization of monomers A and B is initiated by an initiator such as for example a diazoinitiator, preferably azobisisobutyronitrile (AIBN), 2,2'-azobis(2-methylpropionamidine); a peroxide, preferably acyl peroxides, acetyl peroxides, benzoyl peroxides, alkyl peroxides, hydroperoxides, acyl alkylsulfonyl peroxides, dialkyl peroxydicarbonates, diperoxyketals, ketone peroxides; a perester; an azo; a disulfide; a tetrazene; a persulfate compounds. Alternatively, the polymerization of monomers A and B is initiated by a redox reaction.

In one embodiment, the polymerization of monomers A and B is performed in presence of a chain transfer agent (CTA) comprising a moiety -L-R, wherein L and R are as defined above. In one embodiment, the chain transfer agent (CTA) does not comprise a moiety -L-R which is $-S-(CH_2)_2-COOH$.

In one embodiment, the polymerization of monomers A and B is performed in presence of a chain transfer agent (CTA), wherein the CTA is a substituted alkylthiol or a disulfide. Preferably, the alkylthiol or the disulfide is substituted by a group selected from COOH, $NH_2$, PEG, DNA, RNA, PNA, polysaccharide, peptide or any functional group or any bioactive group as defined herein.

In one embodiment, the chain transfer agent (CTA) is not 3-mercaptopropionic acid (MPA).

In one embodiment, the chain transfer agent (CTA) is not a RAFT agent; preferably is not a chain transfer agent selected from trithiocarbonate, dithiocarbamate or dithiobenzoate.

In one embodiment, the chain transfer agent (CTA) is not dibenzyl carbonotrithioate.

In one embodiment, the molar quantity of the initiator is ranging from 0.1 to 15%, preferably from 0.1% to 10%, in moles relative to the molar amount of monomers.

In one embodiment, the molar quantity of the chain transfer agent is different from 0 and is ranging up to 50%, preferably up to 20%. one embodiment, the molar quantity of the chain transfer agent is ranging from $10^{-6}$% to 20%, from $10^{-5}$% to 20%, from $10^{-4}$% to 20%, from $10^{-3}$% to 20%, from $10^{-2}$% to 20%, from 0.1 to 15%, from 1% to 15%, from 2% to 15%, from 5% to 15% in moles relative to the molar amount of monomers. In another embodiment, the molar quantity of the chain transfer agent is 10% in moles relative to the molar amount of monomers. In another embodiment, the molar quantity of the chain transfer agent is 5% in moles relative to the molar amount of monomers.

The invention further relates to a functionalizable or functionalized material. According to one embodiment, the invention relates to a mono-functionalizable or mono-functionalized material. According to another embodiment, the invention relates to a bi-functionalizable or bi-functionalized material.

In an embodiment, the functionalizable/functionalized material of the invention comprises a material and at least one ligand according to the invention. In one embodiment, the material is selected from the group comprising metals, semiconductors, oxides, lanthanides or mixtures thereof. In one embodiment, the material is preferably selected from gold, iron, silver, copper, aluminum, platinum, lead, palladium, iron oxide, titanium dioxide, cerium oxide, metal chalcogenide, metal pnictide, cadmium, zinc, magnesium, mercury, gallium, indium, thallium, cobalt, tin or mixtures thereof.

In a specific embodiment, the material is under the form of particles. In one embodiment, the particles of the invention have the shape of a sphere, a cube, a tetrahedron, a rod, a wire, a platelet, a tube, a cube, a ribbon, or mixture thereof. According to an embodiment, particles are microparticles or nanoparticles, preferably nanoparticles. According to one embodiment, microparticles are microspheres. According to one embodiment, nanoparticles are nanocrystals, preferably under the form of quantum dots.

An object of the invention is thus a nanomaterial comprising a nanocrystal complexed with at least one ligand of the invention.

In one embodiment, said nanocrystal is a 0D, 1D, or 2D nanocrystal.

In one embodiment, said nanocrystal may be for instance a nanosheet, a nanorod, a nanoplatelet, a nanoplate, a nanoprism, a nanowall, a nanodisk, a nanoparticle, a nanowire, a nanopowder, a nanotube, a nanotetrapod, a nanoribbon, a nanobelt, a nanoneedle, a nanocube, a nanoball, a nanocoil, a nanocone, a nanopiller, a nanoflower, or a quantum dot.

In one embodiment, said nanocrystal is inorganic. In another embodiment, said nanocrystal is organic.

In one embodiment, said nanocrystal is a semiconductor material, a ceramic material, a magnetic material or a metallic material.

In one embodiment, said nanocrystal is a semi-conductor selected from group IV, group IIIA-VA, group IIA-VIA, group IIIA-VIA, group IA-IIIA-VIA, group IIA-VA, group WA-VIA, group VIB-VIA, group VB-VIA, or group IVB-VIA.

In one embodiment, said nanocrystal is a material MxEy, wherein:
M is Zn, Cd, Hg, Cu, Ag, Al, Ga, In, Si, Ge, Pb, Sb, Pd, Fe, Au, Ti, Bi, W, Mo, V or a mixture thereof,
E is O, S, Se, Te, N, P, As, or a mixture thereof, and
x and y are independently a decimal number from 0 to 5, at the condition that when x is 0, y is not 0 and inversely.

In one embodiment, said material MxEy comprises cationic elements M and anionic elements E in stoichiometric ratio, said stoichiometric ratio being characterized by values of x and y corresponding to absolute values of mean oxidation number of elements E and M respectively.

In one embodiment, said nanocrystal is a material selected from Si, Ge, CdS, CdSe, CdTe, ZnS, ZnSe, ZnTe, HgS, HgSe, HgTe, PbS, PbSe, PbTe, $CuInS_2$, $CuInSe_2$, $AgInS_2$, $AgInSe_2$, CuS, $Cu_2S$, $Ag_2S$, $Ag_2Se$, $Ag_2Te$, InN, InP, InAs, InSb, $In_2S_3$, $Cd_3P_2$, $Zn_3P_2$, $Cd_3As_2$, $Zn_3As_2$, ZnO, AN, AlP, AlAs, AlSb, GaN, GaP, GaAs, GaSb, $FeS_2$, $TiO_2$, $Bi_2S_3$, $Bi_2Se_3$, $Bi_2Te_3$, $MoS_2$, $WS_2$, $VO_2$, and alloys and mixtures thereof.

In one embodiment, said nanocrystal is a metallic material such as gold, silver, copper, aluminum, iron, platinum, lead, palladium, iron oxide, titanium dioxide, cerium oxide, metal chalcogenide, metal pnictide, cadmium, zinc, magnesium, mercury, gallium, indium, thallium, cobalt, tin or mixtures thereof.

In one embodiment, said nanocrystal presents a heterostructure, which means that the nanocrystal of the invention is partially coated by at least one layer of inorganic material.

A semiconductor nanocrystal is capable of emitting electromagnetic radiation upon excitation (i.e., the semiconductor nanocrystal is luminescent) and includes a "core" of one or more first semiconductor materials, and may be surrounded by a "shell" of a second semiconductor material. A semiconductor nanocrystal core surrounded by a semiconductor shell is referred to as a "core/shell" semiconductor nanocrystal. The surrounding "shell" material will preferably have a bandgap energy that is larger than the bandgap energy of the core material and may be chosen to have an atomic spacing close to that of the "core" substrate.

In one embodiment, the nanocrystal of the invention presents a core/shell structure, i.e. the nanocrystal comprises a core and a shell of semiconducting material.

In one embodiment, the nanocrystal of the invention has a core/shell structure, i.e. the core is totally coated by at least one layer of inorganic material.

Preferably, said quantum dots are core/shell type I quantum dots. Said type I quantum dot can have a band alignment between the core and the shell such that the exciton created in the shell is transferred in the core where it recombines radiatively.

In another embodiment, the nanocrystal of the invention comprises a core totally coated by a first layer of inorganic material, said first layer being partially or totally surrounded by at least one further layer of inorganic material.

In one embodiment, said core and said at least one layer of inorganic material have the same composition or do not have the same composition.

In one embodiment, said core and said at least one layer of inorganic material may be a semi-conductor from group IV, group IIIA-VA, group IIA-VIA, group IIIA-VIA, group IA-IIIA-VIA, group IIA-VA, group IVA-VIA, group VIB-VIA, group VB-VIA, or group IVB-VIA.

In another embodiment, said core and said at least one layer of inorganic material may comprise a material MxEy, wherein:
M is Zn, Cd, Hg, Cu, Ag, Al, Ga, In, Si, Ge, Pb, Sb, Pd, Fe, Au, Ti, Bi, W, Mo, V or a mixture thereof,
E is O, S, Se, Te, N, P, As, or a mixture thereof, and
x and y are independently a decimal number from 0 to 5, at the condition that when x is 0, y is not 0 and inversely.

In another embodiment, said core and said at least one layer of inorganic material may be composed of a material from Si, Ge, CdS, CdSe, CdTe, ZnS, ZnSe, ZnTe, HgS, HgSe, HgTe, PbS, PbSe, PbTe, $CuInS_2$, $CuInSe_2$, $AgInS_2$, $AgInSe_2$, CuS, $Cu_2S$, $Ag_2S$, $Ag_2Se$, $Ag_2Te$, InN, InP, InAs, InSb, $In_2S_3$, $Cd_3P_2$, $Zn_3P_2$, $Cd_3As_2$, $Zn_3As_2$, ZnO, AN, AlP, AlAs, AlSb, GaN, GaP, GaAs, GaSb, $FeS_2$, $TiO_2$, $Bi_2S_3$, $Bi_2Se_3$, $Bi_2Te_3$, $MoS_2$, $WS_2$, $VO_2$, and alloys and mixtures thereof.

In one embodiment, the core and/or the shell can be a semiconductor material including, but not limited to, those of the group II-VI (ZnS, ZnSe, ZnTe, CdS, CdSe, CdTe, HgS, HgSe, HgTe, MgS, MgSe, MgTe, CaS, CaSe, CaTe, SrS, SrSe, SrTe, BaS, BaSe, BaTe, and the like) and III-V (GaN, GaP, GaAs, GaSb, InN, InP, InAs, InSb, and the like) and IV (Ge, Si, and the like) and IV-VI (PbS, PbSe) and I-III-VI-2 ($CuInS_2$, $CuInSe_2$, $AgInS_2$, $AgInSe_2$, $CuGaS_2$, $CuGaSe_2$, $AgGaS_2$, $AgGaSe_2$,) and L2-VI ($Ag_2S$, $Ag_2Se$) and IV-VI-2 ($SnS_2$, $SnSe_2$) and II-V ($Cd_3P_2$) and oxides (ZnO) materials, and an alloy or a mixture thereof.

In another embodiment, the nanocrystal of the invention presents a heterostructure comprising a metallic material and semiconductor material.

According to one embodiment, the functionalizable/functionalized material of the invention comprises:
a material, preferably under the form of particles; and
at least one ligand according to the invention.

According to one embodiment, the material complexed by the ligand of the invention is a nanoparticle, leading to a functionalizable/functionalized nanomaterial.

According to one embodiment, the nanomaterial of the invention comprises:
a nanoparticle, preferably a nanocrystal; and
at least one ligand according to the invention.

According to an embodiment, the nanomaterial of the invention comprises:
a nanoparticle as described above, preferably a nanocrystal; and
at least one ligand according to the invention which is a copolymer of formula (I):

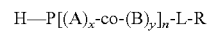

wherein
A represents an anchoring monomer having a side-chain comprising a first moiety $M_A$ having affinity for the surface of a nanocrystal;
B represents a hydrophilic monomer having a side-chain comprising a second moiety $M_B$ being hydrophilic;
n represents a positive integer, preferably an integer ranging from 1 to 1000, preferably from 1 to 499, from 1 to 249 or from 1 to 99;
x and y represent each independently a percentage of n, wherein x and y are different from 0% of n and different from 100% of n, preferably ranging from more than 0% to less than 100% of n, preferably from more than 0% to 80% of n, from more than 0% to 50% of n; wherein x+y is equal to 100% of n;

R represents:
- a functional group selected from the group comprising —$NH_2$, —COOH, —OH, —SH, —CHO, ketone, halide; activated ester such as for example N-hydroxysuccinimide ester, N-hydroxyglutarimide ester or maleimide ester; activated carboxylic acid such as for example acid anhydride or acid halide; isothiocyanate; isocyanate; alkyne; azide; glutaric anhydride, succinic anhydride, maleic anhydride; hydrazide; chloroformate, maleimide, alkene, silane, hydrazone, oxime and furan;
- a bioactive group selected from the group comprising avidin or streptavidin; antibody such as a monoclonal antibody or a single chain antibody; sugars; a protein or peptide sequence having a specific binding affinity for an affinity target, such as for example an avimer or an affibody (the affinity target may be for example a protein, a nucleic acid, a peptide, a metabolite or a small molecule), antigens, steroids, vitamins, drugs, haptens, metabolites, toxins, environmental pollutants, amino acids, peptides, proteins, aptamers, nucleic acids, nucleotides, peptide nucleic acid (PNA), folates, carbohydrates, lipids, phospholipid, lipoprotein, lipopolysaccharide, liposome hormone, polysaccharide, polymers, polyhistidine tags, fluorophores; and L represents a bound or a spacer selected from the group comprising alkylene, alkenylene, arylene or arylalkyl linking groups having 1 to 50 chain atoms, wherein the linking group can be optionally interrupted or terminated by —O—, —S—, —$NR_7$—, wherein $R_7$ is H or alkyl, —CO—, —NHCO—, —CONH— or a combination thereof; or a spacer selected from the group comprising DNA, RNA, peptide nucleic acid (PNA), polysaccharide, peptide.

According to an embodiment, the nanomaterial of the invention comprises:
- a nanocrystal as described above; and
- an outer layer including at least one ligand according to the invention which is a copolymer of formula (I) as described above.

In a preferred embodiment, the nanomaterial of the invention comprises a ligand of formula (I) wherein R is an activated function such as for example and activated ester or an activated carboxylic acid, preferably an activated ester, more preferably N-hydroxysuccinimide ester.

In one embodiment of the invention, the nanomaterial of the invention comprises a nanocrystal complexed by the ligand of formula (II):

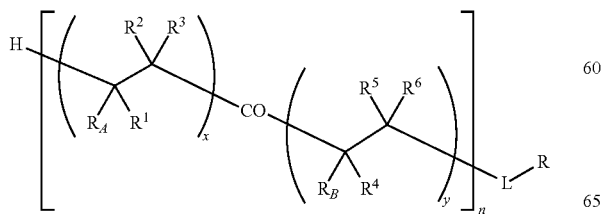

wherein
n, x, y, L and R are as defined in formula (I);
$R_A$ represents a group comprising the first moiety $M_A$ having affinity for the surface of a nanocrystal;
$R_B$ represents a group comprising the second moiety $M_B$ being hydrophilic;
$R^1$, $R^2$, $R^3$, $R^4$, $R^5$ and $R^6$ represent each independently H or a group selected from the alkyl, alkenyl, aryl, hydroxyl, halogen, alkoxy and carboxylate, amide.

In a specific embodiment, the nanomaterial of the invention comprises a nanocrystal complexed by the ligand of formula (I-e'):

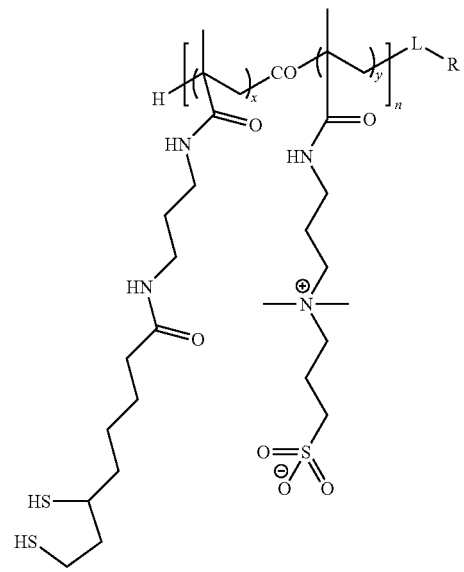

wherein n, x, y, L and R are as defined in formula (I) above.

In a further embodiment, the nanoparticle of the invention comprises a nanocrystal complexed by the ligand of formula (I-f'):

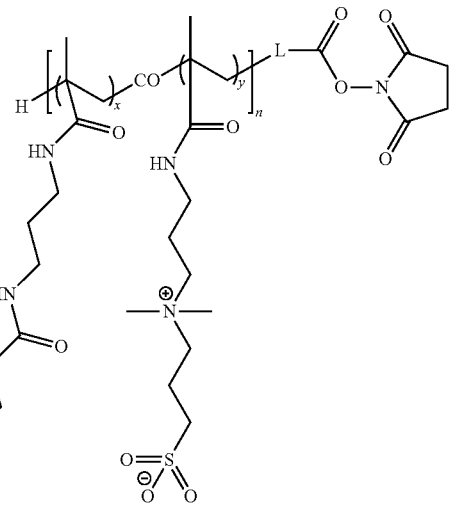

wherein n, x, y and L are as defined in formula (I) above.

In a preferred embodiment, in formula (I-f), L represents an alkylene linking group having 1 to 20 chain atoms and optionally interrupted or terminated by —O— or —S—. More preferably, L is of formula —S—$(CH_2)_{n1}$, wherein $n_1$ is a positive integer ranging from 1 to 20, preferably 1 to 5, more preferably 1, 2 or 3. In another embodiment, L represents an ethylene glycol derivative, preferably of formula —$[CH_2—CH_2—O]_{n2}$—$(CH_2)_{n3}$—S— wherein $n_2$ and $n_3$ are each independently positive integers ranging from 1 to 20, preferably 1, 2, 3, 4, 5, 6 7, 8, 9 or 10, more preferably $n_2$ is equal to 8 and $n_3$ is equal to 2.

In another embodiment of the invention, the nanomaterial of the invention comprises a ligand of formula (I) wherein R is a bioactive group, preferably a protein or an antibody.

Preferred embodiments relative to the ligand of formula (I) of the invention described above apply to the ligand of formula (I) comprised in the nanomaterial of the invention.

According to one embodiment, the nanomaterial of the invention comprises a ligand of formula (I) wherein the number of ligand per dot is ranging from less than 100; preferably less than 50 ligands per dots; more preferably less than 30 ligands per dots. In one embodiment, the number of ligand per dot is about 20 ligands.

According to one embodiment, the nanomaterial of the invention comprises a ligand of formula (I) wherein the number of fluorophores per dot is ranging from less than 100; preferably less than 20; preferably is 1, 2, 3, 4, 5, 6, 7, 8, 9, 10, 11, 12, 13, 14, 15, 16, 17, 18, 19, or 20 fluorophores per dot; preferably is ranging from more than 0 to 1. In one embodiment, the number of fluorophores per dot is 0.5.

Another object of the invention is a method for complexing at least one ligand of the invention to at least one material, preferably at least one nanoparticle, more preferably at least one nanocrystal, comprising:
optionally a first step of complexation of the material, preferably nanoparticles, more preferably nanocrystals, with an intermediate ligand being a weakly binding ligand or a small molecule (Meerwein's salt) ensuring the homogeneous dispersion of the nanocrystal into a solvent miscible in part with water,
a step of monophasic exchange at about 40° C. to about 100° C. in an aqueous medium overnight to remove the weak intermediate ligand and replace it by the ligand of the invention.

In one embodiment, said weakly binding ligand or molecule may be MPA, or trimethylsilylating agents, or trialkyl oxonium salts (Meerwein's salt), or any monothiol, or amine ligands.

In one embodiment, said first step is performed in basic chloroform and leads to the precipitation of the nanocrystal complexed to the intermediate ligand and to the homogeneous dispersion of the nanocrystal into water at room temperature. In another embodiment, said first step is performed in ethanol and leads to the precipitation of the nanocrystal complexed to the intermediate ligand.

In one embodiment, said second step is performed in an aqueous medium such as 20 mM aqueous NaCl at about 50° C. to 75° C., preferably 60° C., overnight, to remove the weak intermediate ligand and replace it by the ligand of the invention.

In another embodiment, said method may further comprise an ultrafiltration step and then an ultracentrifugation step in an aqueous sucrose gradient.

In the case wherein R represents a functional group in the ligand of formula (I), the process for manufacturing the nanomaterial of the invention may further comprise a subsequent step of bio-conjugation to introduce a bioactive group at the end of the polymeric chain of the ligand.

In a further embodiment, some of the $M_A$ moieties of the anchoring monomers A of the ligand of the invention may be functionalized by bioactive groups, once the ligand has been complexed to the nanocrystal.

In an embodiment, the process for manufacturing the nanomaterial of the invention comprises:
optionally a first step of complexation of nanocrystals with an intermediate ligand being a weakly binding ligand or a small molecule (Meerwein's salt) ensuring the homogeneous dispersion of the nanocrystal into a solvent miscible in part with water;
a step of monophasic exchange at about 40° C. to about 100° C. in an aqueous medium overnight to remove the weak intermediate ligand and replace it by the ligand of the invention;
optionally one or more subsequent steps selected from:
in the case wherein R represents a functional group in the ligand of formula (I), a step of bio-conjugation to introduce a bioactive group at the end of the polymeric chain of the ligand;
functionalization of some of the $M_A$ moieties of the anchoring monomers A of the ligand by bioactive groups.

By "some of the $M_A$ moieties of the anchoring monomers" it is referred to less than 70% of the total number of $M_A$ moieties.

The nanomaterial of the invention may be obtained by the complexation of the ligand of formula (I) of the invention with a nanocrystal. Once complexed with the nanocrystal, the ligand of formula (I) may be modified, especially by activation of functional group R present at one end of the ligand. Moreover, the ligand of formula (I) may be modified by conjugation of a bioactive group to the functional group or activated functional group present at one end of the ligand, leading to functionalized ligand of formula (I).

According to one embodiment, the nanomaterial of the invention is activated by modifying the terminal end R of the ligand of formula (I) under the form of a terminal N-hydroxysuccinimide ester. Such activation enables the conjugation of bioactive groups comprising an amino group.

Another object of the invention is a water-soluble composition comprising at least one quantum dot, nanoplatelet or quantum dot having its lateral dimensions larger than its thickness, complexed with at least one ligand of the invention.

Another object of the invention is the use of said quantum dot, nanoplatelet or quantum dot having its lateral dimensions larger than its thickness, complexed with at least one ligand of the invention for bioimaging, biotargeting, medical imaging, biosensing.

Thus, it is readily apparent that said complexes find use in a variety of assays where other, less reliable, labeling methods have typically been used, including, without limitation, fluorescence microscopy, fluorescence histology, fluorescence cytology, fluorescence pathology, cell labeling, flow cytometry, western blotting, Fluorescence Resonance Energy Transfer (FRET), immunocytochemistry, Fluorescence In Situ Hybridization (FISH) and other nucleic acid hybridization assays, signal amplification assays, DNA and protein sequencing, immunoassays such as competitive binding assays and ELISAs, immunohistochemical analysis, protein and nucleic acid separation, homogeneous assays, multiplexing, high throughput screening, chromosome karyotyping, and the like.

EXAMPLES

Figure 1A:
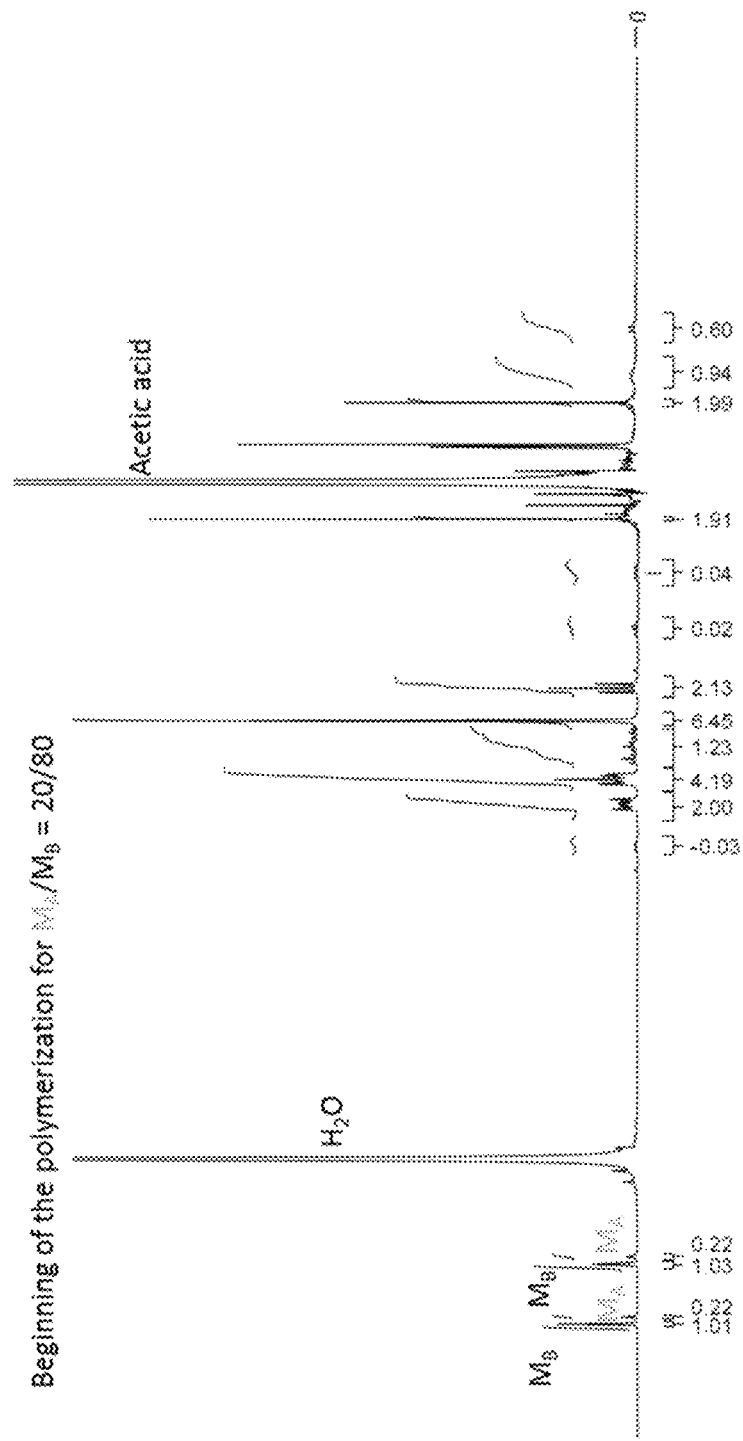
FIGS. 1A and 1B are $^1$H NMR spectra recorded in $D_2O$ showing the monomer consumption during the polymer synthesis, between the initial state of the polymerization (FIG. 1A) and the end of the polymerization (FIG. 1B).

The present invention will be better understood with reference to the following examples. These examples are intended to representative of specific embodiments of the invention, and are not intended as limiting the scope of the invention.

Abbreviations

AIBN: azobisisobutyronitrile;
APMA.HCl: N-(3-aminopropyl)methacrylamide hydrochloride;
CTA: Chain Transfer Agent;
DCC: dicyclohexylcarbodiimide;
EDC: 1-Ethyl-3-[3-dimethylaminopropyl]carbodiimide hydrochloride;
LA: 5-(1,2-dithiolan-3-yl)pentanoic acid, also known as lipoic acid;
MES buffer: 2-(N-morpholino)ethanesulfonic acid aqueous buffer;
MFA: N-methylformamide;
MPA: 3-mercaptopropionic acid;
NHS: N-Hydroxysuccinimide;
PEG: poly(ethylene glycol);
QD(s): Quantum Dot(s);
SA: streptavidin;
SPP: 3-sulfopropyldimethyl-3-methacrylamidopropylammonium inner salt.

Materials and Instrumentation

Streptavidin was purchased from Biospa; APMA.HCl was purchased from Tebu-bio; SPP and 3-[3-methacrylamidopropyl-(dimethyl)ammonio]propane-1-sulfonate), from Raschig GmbH (RaleMer SPP); all other chemicals used therein were purchased from Sigma-Aldrich. All of these purchased chemicals were used without further purification unless otherwise specified. Chromatography on silica was carried out on Kieselgel 60 (230-240 mesh, Merck) and analytical TLC was performed on Merck precoated silica gel (60 $F_{254}$) $^1$H NMR spectrum was recorded on a Bruker Avance DPX 400 spectrometer at 400.13 MHz. Chemical shifts (δ) are expressed in ppm and coupling constant (J) in hertz. Absorption measurements were carried out with a Cary 5E UV-vis-NIR spectrophotometer (Varian).

Example 1

Ligand Synthesis

Synthesis of monomer A (5-(1,2-dithiolan-3-yl)-N-(3-methacrylamidopropyl)-pentanamide)

To a suspension of APMA.HCl (2 g, 11.2 mmol) in dichloromethane (20 mL) was added triethylamine (2.5 mL, 17.9 mmol). Methanol (2 mL) was introduced to obtain complete solubilization. A solution of LA (2.76 g, 13.4 mmol) in dichloromethane (5 mL) was then added, followed by NHS (1.58 g, 13.8 mmol) in one portion. The reaction mixture was cooled down to 0° C. with an ice bath and a solution of DCC (3.00 g, 14.4 mmol) in dichloromethane (10 mL) was injected dropwise. The medium was warmed up to room temperature and further stirred overnight. A pale yellow solution containing a white precipitate was obtained. The solution was washed by a 0.1 M aqueous HCl solution (2×50 mL), deionized water (1×50 mL) and a 0.2 M aqueous NaOH solution (2×50 mL). The organic phase was separated, dried over MgSO$_4$, filtrated and concentrated under reduced pressure. The crude residue was purified by chromatography on silica (eluent: hexane/ethyl acetate 1/4, then hexane/acetone 1/1) to give A (2.88 g, 8.71 mmol, 78%) as a pale yellow solid. $R_f$=0.37 (hexane/acetone 1/1); $^1$H NMR (CDCl$_3$, 400 MHz): δ 7.03 (sl, 1H); 6.87 (sl, 1H); 5.72 (s, 1H); 5.29 (s, 1H); 3.53-3.39 (m, 1H); 3.29-3.20 (m, 4H); 3.14-3.01 (m, 2H); 2.43-2.35 (m, 1H); 2.18 (t, J=8.0 Hz, 2H); 1.92 (s, 3H); 1.88-1.80 (m, 1H); 1.68-1.55 (m, 6H); 1.48-1.33 (m, 2H).

Synthesis of the Ligand

The polymerization step consisted of the radical copolymerization of two methacrylamides: one containing the precursor of a dithiol anchoring function (monomer A, obtained as described above), the other including a sulfobetaine group (monomer B, SPP commercially available).

Due to mismatching monomers' solubilities, the solvent used for these polymerizations was acetic acid. Various A/B molar ratios have been tested between 10/90 and 50/50.

The amounts of initiating agent AIBN (2,2'-Azobis(2-methylpropionitrile)) and of CTA were chosen in various molar equivalents relative to the total amount of monomers, in order to form various length chains. Various monomer/CTA molar ratios have been tested between 10/1 and 40/1.

The monomers conversion rates were determined by $^1$H NMR in $D_2O$ (classically over 90%).

Figure 1B:
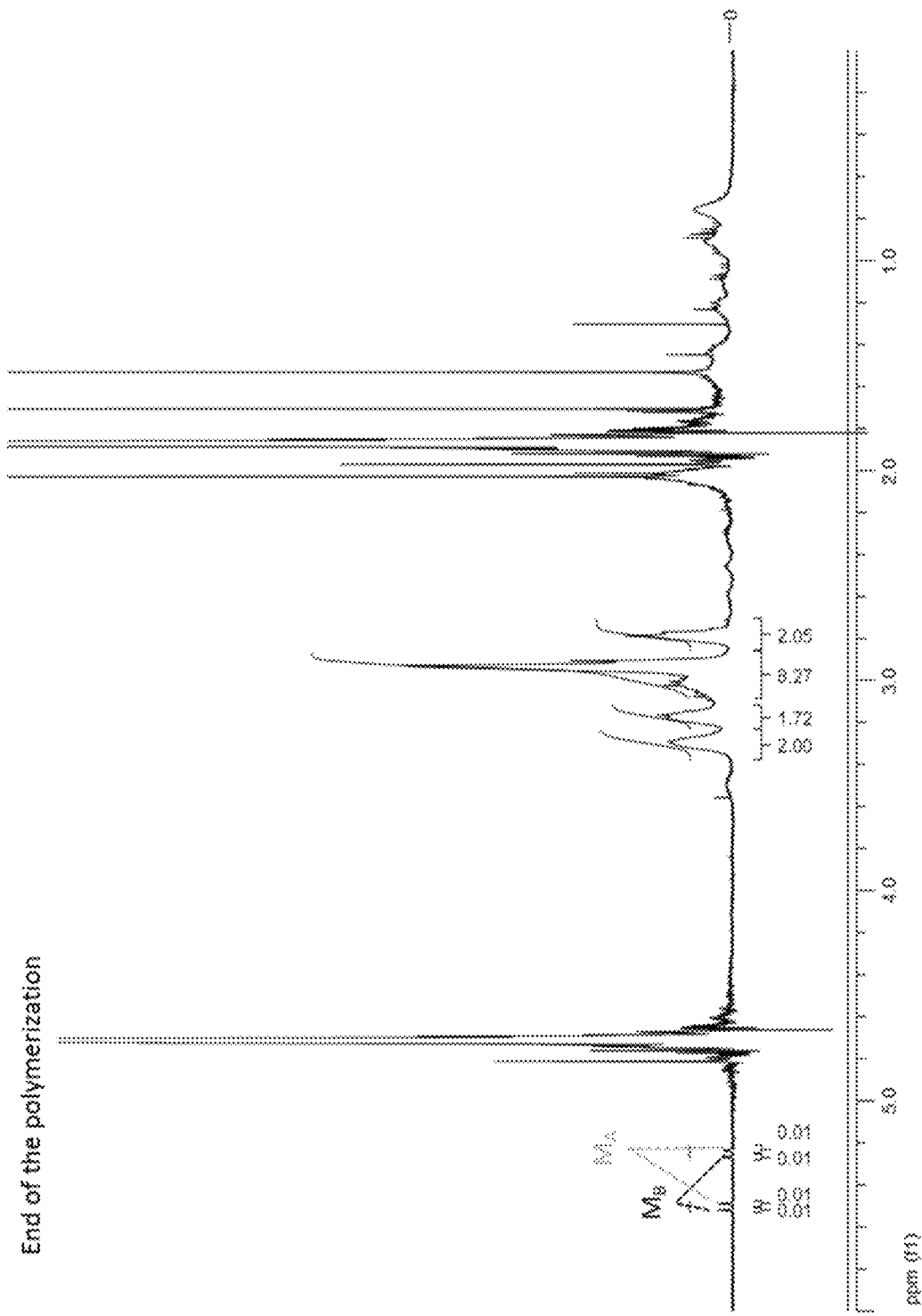

Characterization of the products by NMR confirmed the $M_A/M_B$ molar ratio by comparison of the acrylamide peaks between the initial state of the polymerization (FIG. 1A) and the end of the polymerization (FIG. 1B).

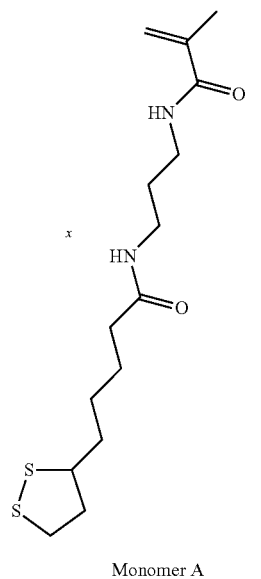

Monomer A 5-(1,2-dithiolan-3-yl)-N-(3-methacryl amidopropyl)pentanamide

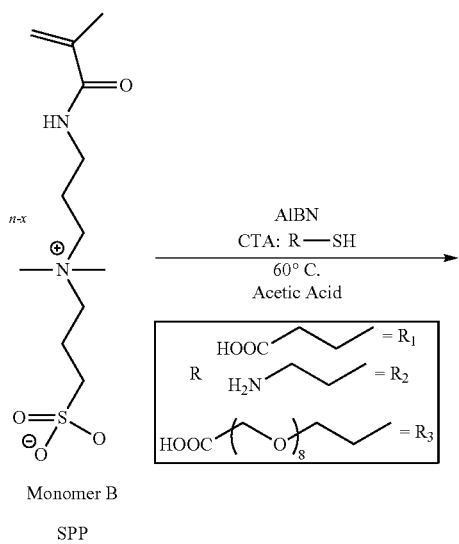

Monomer B

SPP

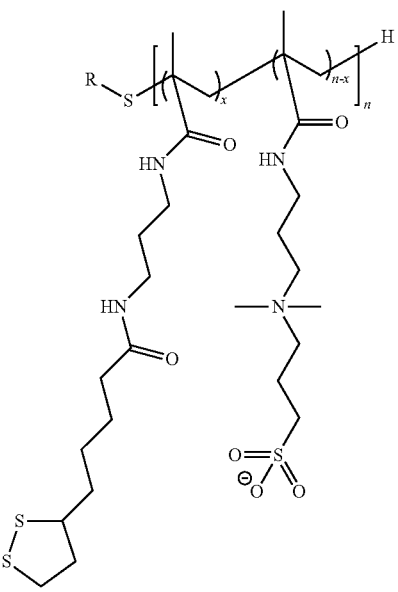

A general procedure is given for the synthesis a ligand with x=2 and n=10.

Monomer B (SPP, 1.17 g, 4 mmol, 4 equiv.), monomer A (5-(1,2-dithiolan-3-yl)-N-(3-methacrylamidopropyl)pentanamide, 331 mg, 1 mmol, 1 equiv.) and CTA (0.5 mmol, 0.5 equiv.) were dissolved in acetic acid (20 mL) in a sealed septum flask. The mixture was degassed with argon and then heated at 60° C. A solution of AIBN (82 mg, 0.5 mmol, 0.5 equiv.) in acetic acid (2 mL) under argon atmosphere was further added in one portion. The mixture was stirred overnight at 60° C. Acetic acid was evaporated under reduced pressure. To remove residual acetic acid traces, the residue was dissolved in 20 mL of deionized water and evaporated under reduced pressure (two times). The residue was then dissolved in 20 mL of deionized water and extracted three times with 20 mL of dichloromethane. The aqueous phase was precipitated in 9-fold excess of ethanol. The precipitated polymer was separated by centrifugation (50 mL centrifuge tubes, 2500 rpm, 10 min), washed 2 times with ethanol and then dried overnight under vacuum. The polymer was obtained as a yellow-brown solid (950 mg, 61%).

| Chain Transfer Agents (CTA) | 0.5 mmol | Structures |
|---|---|---|
| Mercaptopropionic acid (MPA) | 42 µL | HOOC~~~SH |
| Cysteamine | 38 mg | $H_2N$~~~SH |
| O-(2-carboxyethyl)-O'-(2-mercaptoethyl) heptaethylene glycol | 229 mg | HOOC(~~O)$_8$~~SH |

In the case wherein the ligand is obtained by polymerization with "mercapto-carboxilic acid containing compounds" as CTA, the ligand is referred to as "ligandCOOH". Especially, in the case wherein the ligand is obtained by polymerization with mercaptoproprionic acid as CTA, the ligand is referred to as "ligand-$(CH_2)_2COOH$" and in the case wherein the ligand is obtained by polymerization with a CTA comprising a PEG moiety, the ligand is referred to as "ligand-PEG-COOH".

In the case wherein the ligand is obtained by polymerization with "mercapto-amino containing compounds" as CTA, the ligand is referred to as "ligandNH$_2$".

Example 2

Quantum Dot Synthesis

CdSe/CdS/ZnS QDs Synthesis 600-nm-emitting CdSe/CdS/ZnS QDs were synthesized using slight modifications of previously published procedures. CdSe cores were synthesized by reaction of trioctylphosphine selenide and cadmium oleate in octadecene, oleylamine and trioctylphosphine oxide. Three monolayers of CdS shell, followed by two monolayers of ZnS, were grown using cadmium oleate, zinc oleate and sulfur diluted in octadecene following the SILAR (Successive Ionic Layer Adsorption and Reaction) procedure.

Example 3

Nanocrystal Complexation

Ligand Exchange: Standard Procedure

"Classical" biphasic cap exchange with CdSe/CdS/ZnS core/shell QDs solubilized in chloroform did not succeed. The poor solubility of the ligand of the invention in chloroform and the low partition coefficient between the two solvents could explain the difficult phase transfer of the QDs.

To overcome this problem, a two-step process was chosen. A first exchange was performed using pure mercaptopropionic acid (MPA), on as-synthesized QDs precipitated in ethanol. The QDs were kept overnight at 60° C. in order to have QDs surface was saturated by MPA. The excess of MPA was removed and QDs were dispersed in DMF. The MPA were then deprotonated using a large excess of tert-butoxide. The QDs became then instable in organic solvents and were precipitated and washed with ethanol. QDs were then suspended in a sodium tetraborate (pH 9, 10 mM) water-based buffer. To this homogeneous dispersion, an aqueous solution of previously reduced ligand of the invention (by NaBH$_4$) was added to perform the second ligand exchange. The aqueous medium was kept overnight at 60° C. to move from the weak intermediate QD covered by MPA to QD-ligand. The polymer excess was removed by Vivaspin® filtration. The QD-ligand did not show any change in quantum yield after the ligand exchange.

General Procedure

CdSe/CdS/ZnS core/shell QDs in hexane (0.2-2 nmol respectively for 650-550 nm QDs) were precipitated with ethanol (0.5 mL) and centrifuged (13000 rpm, 5 min). The supernatant was removed. The QDs were dispersed in 3-mercaptopropionic acid (MPA) (0.2 mL). The mixture was sonicated to obtain a homogenous dispersion. The QDs dispersion was stored at 60° C. overnight to perform first cap exchange. The QDs were centrifuged (13000 rpm, 2 min) and the MPA phase was discarded. The QDs were dispersed in DMF (0.2 mL) under sonication. 2 mg of potassium tert-butoxide were added and QDs dispersion was sonicated (1 min). The mixture was centrifuged (13000 rpm, 2 min). The uncolored DMF phase was discarded. The precipitated QDs were washed twice with ethanol (2×0.5 mL EtOH). The QDs were dispersed in sodium tetraborate (pH9 10 mM). Typically, at this step, QDs colloidal dispersion was clear. 200 µL of aqueous solution of the ligand of the invention (10 mg/mL), previously reduced 30 min with NaBH$_4$ (1 mg/mg of polymer), were added to QDs dispersion. The aqueous QDs dispersion was stored at 60° C. overnight to perform the second cap exchange. The excess of free ligand and reagents were removed by three washing by membrane ultrafiltration (Sartorius Vivaspin®500 µL disposable filter—cutoff 100 kDa) at 13000 rpm in 20 mM aqueous NaCl. QDs-ligand were finally taken up in 20 mM aqueous NaCl.

In the case wherein the ligand is a ligandCOOH, as in example 1, resulting coated QDs are referred to as "QDs-ligandCOOH".

Example 4

Activation of the Ligand on the Nanocrystal

In the case wherein the ligand of the invention is obtained by polymerization with "mercapto-carboxilic acid containing compounds" as CTA (for example: mercaptopropionic acid or O-(2-Carboxyethyl)-O'-(2-mercaptoethyl)heptaethylene glycol), an acidic function is advantageously introduced at one extremity of the ligand (respectively "ligand (CH$_2$)$_2$COOH" and "ligand-PEG-COOH").

Ligand exchange using these ligandCOOH has been studied in order to provide biocompatible coated QDs presenting carboxylic acidic function, QDs-ligandCOOH. First, reactive N-hydroxysuccinimide (NHS) esters thereof ("QD-ligandNHS") were prepared and purified. Then, these activated QDs have been used to functionalize QDs with protein (for example: streptavidin or antibodies).

Washing Before Freeze-Drying: Standard Procedure

QDs-ligandCOOH in 20 mM aqueous NaCl were washed three times by membrane ultrafiltration at 13000 rpm using a Sartorius Vivaspin®500 µL disposable filter (cutoff 100 kDa) in pure water. QDs-ligandCOOH were finally taken up in pure water for freeze-drying.

Activation of the Carboxylic Acidic Function of the Polymer on QDs: Standard Procedure Freeze-dried QD-ligandCOOH (2.5 mg) were dispersed in pure water (50 µL) at room temperature. In parallel, EDC (5 mg, 30 µmol) and NHS (5 mg, 44 µmol) were dissolved in MES buffer 0.2 M pH 5.5 (1 mL). 20 µL of this solution are added to the dispersion of QD and immediately after 180 µL of MFA are added. The reaction was stirred overnight at room temperature before precipitation in acetonitrile (1 mL). The colored precipitate obtained after centrifugation (13000 rpm, 2 min) was washed twice in acetonitrile (1 mL) before drying under vacuum. QDs-ligandNHS were conserved under inert atmosphere at −18° C.

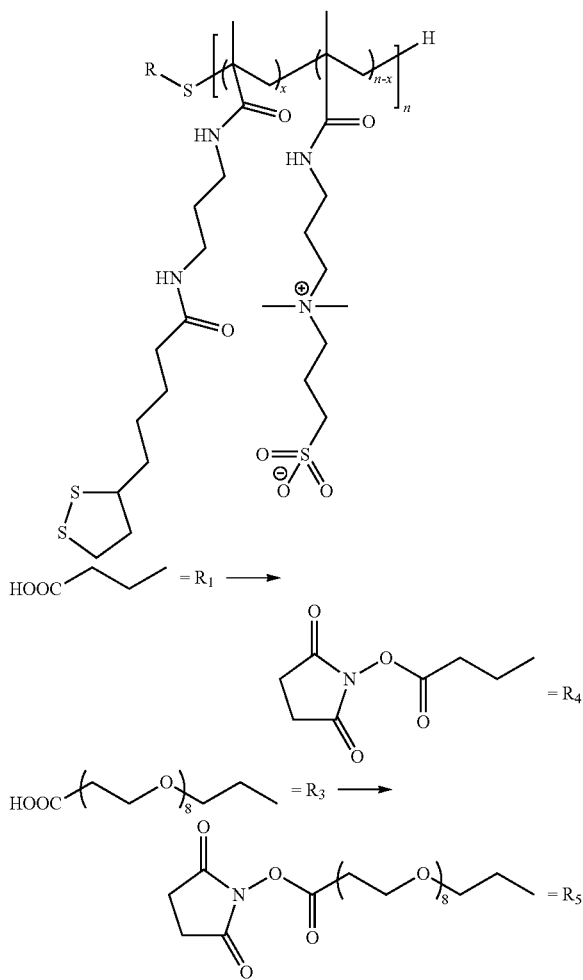

Biomolecules Functionalization of QDs:

Several experiments were carried out starting from either QDs-ligand-COOH or QDs-ligand-NHS.

QDs-ligand-$(CH_2)_2$—COOH represents quantum dots coated with a ligand copolymer wherein the end carboxylic function is from 3-mercaptopropionic acid. QDs-ligand-$(CH_2)_2$—NHS correspond to the corresponding dots after the reaction with N-hydroxysuccinimide.

QDs-ligand-PEG-COOH represents quantum dots coated with a ligand copolymer wherein the end carboxylic function is from a CTA comprising a PEG moiety; especially from (2-carboxyethyl)-O'-(2-mercaptoethyl)heptaethylene glycol. QDs-ligand-PEG-NHS corresponds to the corresponding dots after the reaction with N-hydroxysuccinimide.

Standard Procedure from QDs-ligandNHS

Dried QDs-ligandNHS (2.5 mg) were dispersed in 120 μL streptavidine or antibody solution (10 mg/mL in aqueous NaHCO$_3$ 0.2 M pH 8.4). Protein excess was eliminated by ultracentrifugation on sucrose gradient (40%-10%). QDs-proteins/QDs-antibody were finally taken up in 0.2M aqueous NaHCO$_3$.

Characterizations Biotin Test

Figure 2A:
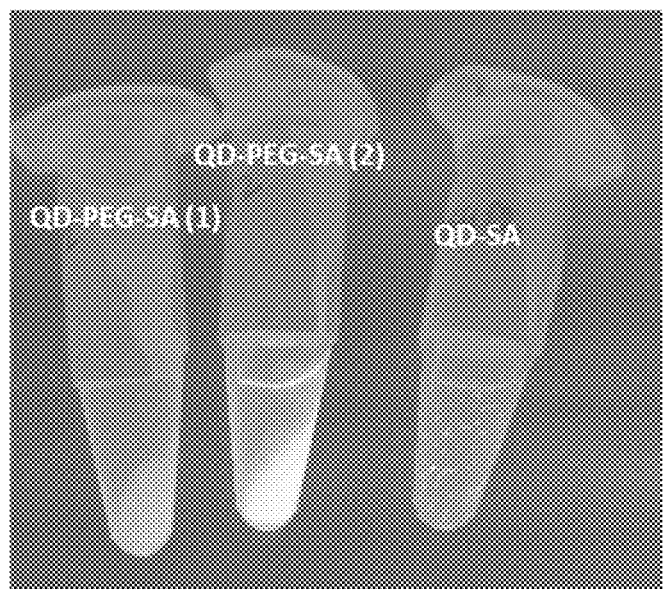
FIGS. 2A et 2B are photographs of coated dots QD-PEG-SA, QD-SA and QD-PEG-COOH observed without any apparatus after reaction with biotin-coated agarose beads.
Figure 2B:
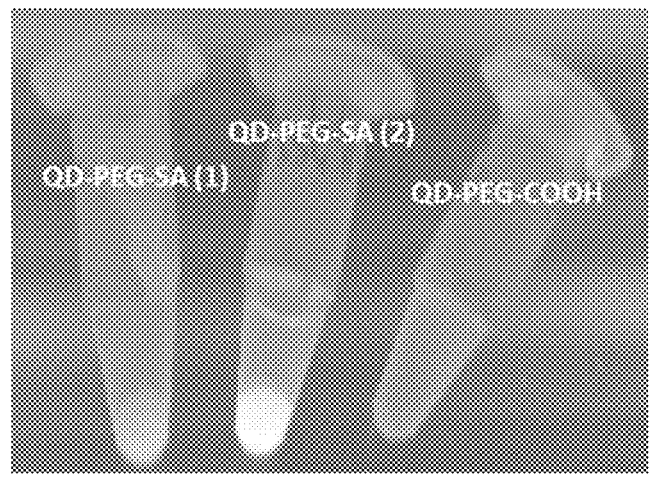
FIG. 2C is a photograph of coated dots QD-PEG-SA, QD-SA and QD-PEG-COOH observed by microscopy after reaction with biotin-coated agarose beads.
Figure 2C:
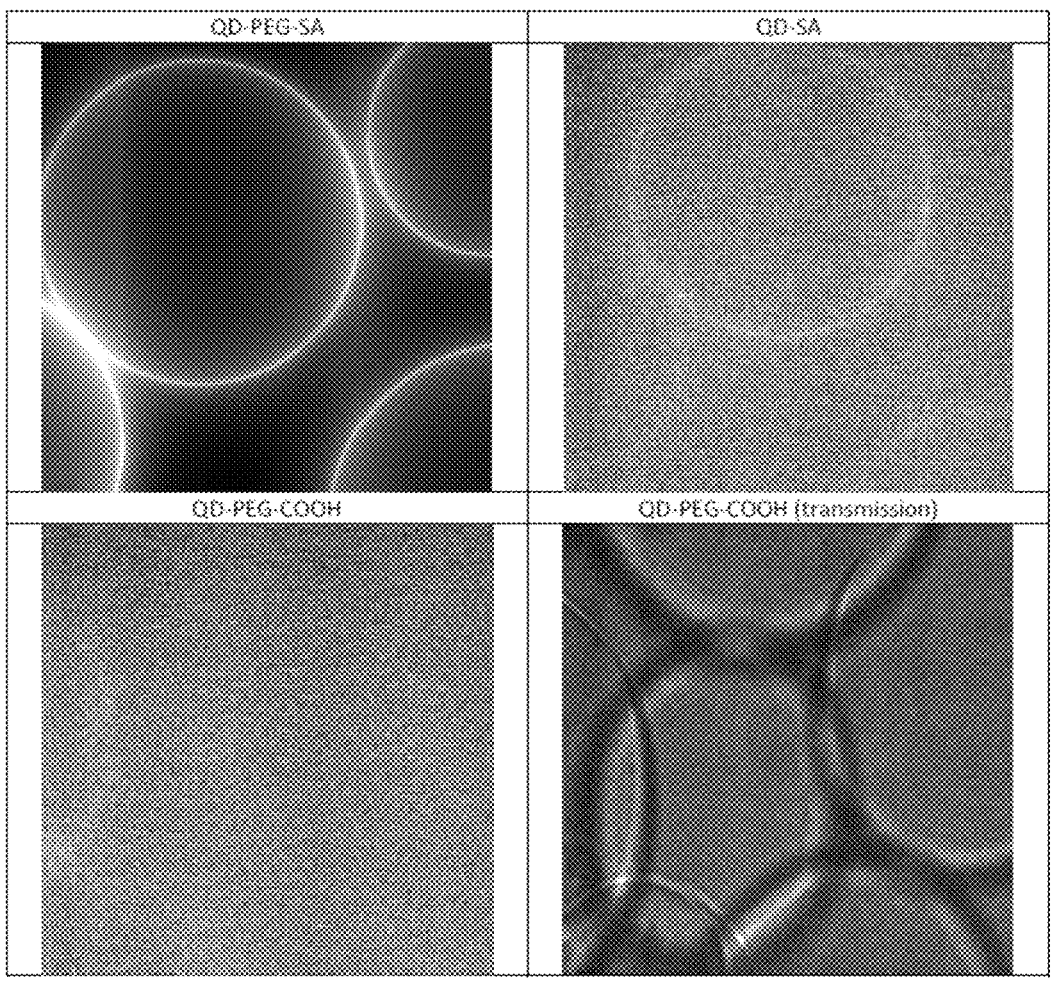

First the quantum dots functionalized by streptavidin were tested with biotin-coated agarose beads in order to evaluate the achievement of the functionalization. The results are shown Table 1 and FIGS. 2A, 2B and 2C.

TABLE 1

Results of the test on biotin-coated agarose beads.

| Reagent 1 (coated quantum dots) | Reagent 2 (protein-NH$_2$) | Obtained product | Reaction with biotin-coated agarose beads* |
|---|---|---|---|
| QDs-ligand-PEG-COOH | Streptavidin | QDs-PEG-SA | + |
| QDs-ligand-$(CH_2)_2$—COOH | Streptavidin | QDs-SA | 0 |
| QDs-ligand-PEG-COOH | — | QDs-PEG-COON | 0 |
| QDs-ligand-$(CH_2)_2$—COOH | — | QDs-$(CH_2)_2$—COOH | 0 |

*+: positive result;
0: negative result

In this test, the high affinity between streptavidin and biotin leads to fluorescence.

The results of Table 1 show that when quantum dots are coated with a ligand comprising a PEG moiety (QDs-ligand-PEG-COOH), their functionalization with streptavidin leads to fluorescent agarose beads (+).

In the case wherein quantum dots are coated with a ligand comprising a —S—$(CH_2)_2$—COOH end obtained from mercaptopropionic acid (QDs-ligand-$(CH_2)_2$—COOH), the reaction between the resulting quantum dots and the agarose beads does not lead to fluorescent beads.

These results show that when the ligand is ended by —S—$(CH_2)_2$—COOH, the functionalization with streptavidin fails whereas in the case wherein the ligand comprises a PEG moiety, the functionalization of the QDs-PEG-COOH is successfully achieved.

Without willing to be bound by a theory, the Applicant thinks that the size of the spacer affects the functionalization of the coated-quantum dots. The skilled human in the art knows that carboxylic function has good affinity for the surface of dots. Thus, increasing the size of the spacer L would have favored the coiling of the end of the ligand chain on the dots surface, preventing the functionalization by a protein, a fluorophore or an antibody.

Unexpectedly, these experiments show that an enough long spacer is required to implement the functionalization of the QDs-NHS with a protein or an antibody.

Number of Fluorophores by Quantum Dot

Functionalized quantum dots were analyzed by HPLC with an absorbance detector at 254 nm or a fluorescence detector (emission parameters: $L_{exc.}$=630 nm and LF=650 nm). The number of fluorophores grafted on a quantum dots is calculated by the ratio between the absorption band of QDs (at 350 nm) and the absorption band of fluorophores (at 650 nm).

The results are shown in the following table:

| Functionalized QDs | Number of fluorophores (F) by QD |
|---|---|
| QDs-PEG-F | 0.5 |
| QDs-F | 0 |

These results show that when quantum dots are coated with a ligand comprising a -PEG-COOH moiety and then functionalized with a fluorophore (QDs-PEG-F), the functionalization reaction is successfully carried out and the average number of flurophores per dot is 0.5.

In the case wherein quantum dots are coated with a ligand comprising a —(CH2)2-COOH end and then functionalized with a fluorophore (QDs-F), the reaction of functionalization fails.

In conclusion, these results confirm that the design of the ligand end is important. Especially, a too short spacer L does not allow the functionalization of the ligand-coated QDs.

The invention claimed is:

1. A nanomaterial comprising:
a nanoparticle; and
at least one ligand which is a copolymer of formula (I):

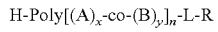

wherein
H represents a hydrogen atom;
co means copolymer;
Poly[(A)$_x$-co-(B)$_y$]$_n$ designates a copolymer with a total of n monomers, a percentage x of said n monomers is monomer A and a percentage y of said n monomers is monomer B, wherein:
monomer A represents an anchoring monomer having a side-chain comprising a first moiety $M_A$ having affinity for the surface of a nanocrystal comprising a metal;
monomer B represents a hydrophilic monomer having a side-chain comprising a second moiety $M_B$ being hydrophilic;
n represents a positive integer;
x and y are different from 0% of n and different from 100% of n; wherein x+y is equal to 100% of n;
R represents:
a functional group selected from the group consisting of —NH$_2$, —COOH, —OH, —SH, —CHO, ketone, halide, activated ester, activated carboxylic acid, isothiocyanate, isocyanate, alkyne, azide, glutaric anhydride, succinic anhydride, maleic anhydride; hydrazide; chloroformate, maleimide, alkene, silane, hydrazone, oxime and furan; or
a bioactive group selected from the group consisting of avidin, streptavidin, antibody, sugars, and a protein or peptide sequence having a specific binding affinity for an affinity target; and
L represents a spacer which is an ethylene glycol derivative of formula —[CH$_2$—CH$_2$—O]n$_2$-(CH$_2$)n$_3$-S— wherein n$_2$ and n$_3$ are each independently positive integers and n$_2$+n$_3$ is higher than 2 and wherein L is linked to Poly[(A)$_x$-co-(B)$_y$]$_n$ through the S atom of —[CH$_2$—CH$_2$—O]n$_2$-(CH$_2$)n$_3$-S— group.

2. The nanomaterial according to claim 1, wherein said nanoparticle is a nanocrystal and wherein the nanocrystal is a 0D, 1D, or 2D nanocrystal.

3. The nanomaterial according to claim 1, wherein said nanoparticle is selected from the group consisting of a nanosheet, a nanorod, a nanoplatelet, a nanoplate, a nanoprism, a nanowall, a nanodisk, a nanoparticle, a nanowire, a nanopowder, a nanotube, a nanotetrapod, a nanoribbon, a nanobelt, a nanoneedle, a nanocube, a nanoball, a nanocoil, a nanocone, a nanopiller, a nanoflower, and a quantum dot.

4. The nanomaterial according to claim 1 wherein the ligand is of formula (II):

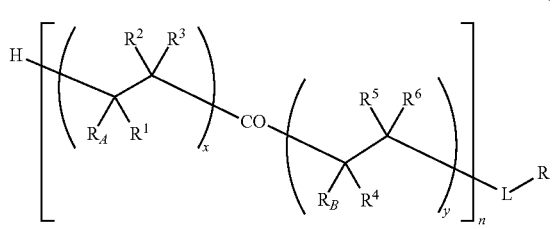

wherein
co, n, x, y, L and R are as defined in claim 1;
$R_A$ represents a group comprising the first moiety $M_A$ having affinity for the surface of a nanocrystal comprising a metal;
$R_B$ represents a group comprising the second moiety $M_B$ being hydrophilic;
$R^1$, $R^2$, $R^3$, $R^4$, $R^5$ and $R^6$ represent each independently H or a group selected from the group consisting of alkyl, alkenyl, aryl, hydroxyl, halogen, alkoxy, carboxylate, and amide.

5. The nanomaterial according to claim 1, wherein the ligand is of formula (I-e'):

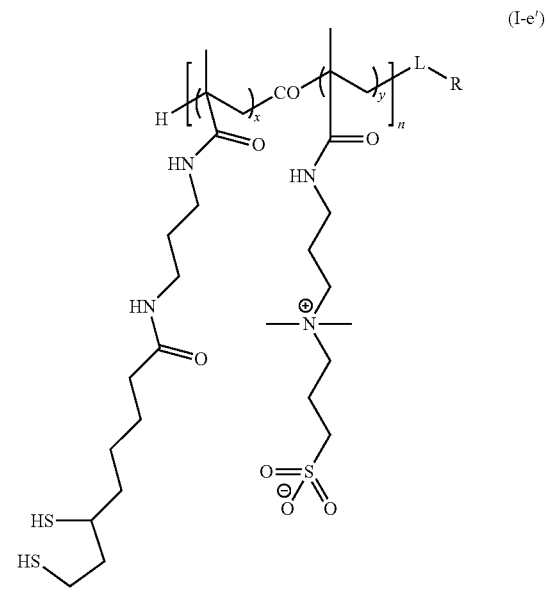

wherein co, n, x, y, L and R are as defined in claim 1.

6. The nanomaterial according to claim 1, wherein the ligand is of formula (I-f'):

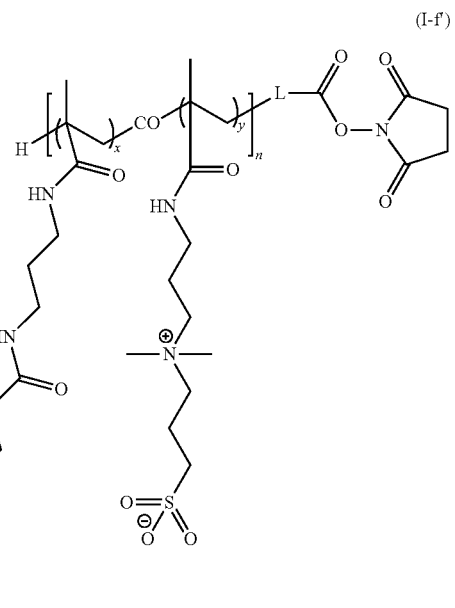

wherein co, n, x, y and L are as defined in claim 1.

7. A water-soluble composition comprising nanomaterials comprising:
   a nanoparticle; and
   at least one ligand which is a copolymer of formula (I):

H-Poly[(A)$_x$-co-(B)$_y$]$_n$-L-R wherein
   H represents a hydrogen atom;
   co means copolymer;
   Poly[(A)$_x$-co-(B)$_y$]$_n$ designates a copolymer with a total of n monomers, a percentage x of said n monomers is monomer A and a percentage y of said n monomers is monomer B, wherein:
      monomer A represents an anchoring monomer having a side-chain comprising a first moiety M$_A$ having affinity for the surface of a nanocrystal comprising a metal;
      monomer B represents a hydrophilic monomer having a side-chain comprising a second moiety M$_B$ being hydrophilic;
   n represents a positive integer;
   x and y are different from 0% of n and different from 100% of n; wherein x+y is equal to 100% of n;
   R represents:
   a functional group selected from the group consisting of —NH$_2$, —COOH, —OH, —SH, —CHO, ketone, halide, activated ester, activated carboxylic acid, isothiocyanate, isocyanate, alkyne, azide, glutaric anhydride, succinic anhydride, maleic anhydride, hydrazide, chloroformate, maleimide, alkene, silane, hydrazone, oxime and furan; or
   a bioactive group selected from the group consisting of avidin, streptavidin, antibody, sugars, and a protein or peptide sequence having a specific binding affinity for an affinity target; and
   L represents a spacer which is an ethylene glycol derivative of formula —[CH$_2$—CH$_2$—O]n$_2$-(CH$_2$)n$_3$-S— wherein n$_2$ and n$_3$ are each independently positive integers and n$_2$+n$_3$ is higher than 2 and wherein L is linked to Poly[(A)$_x$-co-(B)$_y$]$_n$ through the S atom of —[CH$_2$—CH$_2$—O]n$_2$-(CH$_2$)n$_3$-S— group.

8. A method for manufacturing the nanomaterial according to claim 1 comprising:
   a first step of complexation of nanocrystals with an intermediate ligand being a weakly binding ligand or a small molecule ensuring the homogeneous dispersion of the nanocrystal into a solvent miscible in part with water;
   a step of monophasic exchange at about 40° C. to about 100° C. in an aqueous medium overnight to remove the weak intermediate ligand and replace it by the ligand which is a copolymer of general formula (I):

H-Poly[(A)$_x$-co-(B)$_y$]$_n$-L-R wherein
   H represents a hydrogen atom;
   co means copolymer;
   Poly[(A)$_x$-co-(B)$_y$]$_n$ designates a copolymer with a total of n monomers, a percentage x of said n monomers is monomer A and a percentage y of said n monomers is monomer B, wherein:
      monomer A represents an anchoring monomer having a side-chain comprising a first moiety M$_A$ having affinity for the surface of a nanocrystal comprising a metal;
      monomer B represents a hydrophilic monomer having a side-chain comprising a second moiety M$_B$ being hydrophilic;
   n represents a positive integer;
   x and y are different from 0% of n and different from 100% of n, wherein x+y is equal to 100% of n;
   R represents:
   a functional group selected from the group consisting of —NH$_2$, —COOH, —OH, —SH, —CHO, ketone, halide, activated ester, activated carboxylic acid, isothiocyanate, isocyanate, alkyne, azide, glutaric anhydride, succinic anhydride, maleic anhydride, hydrazide, chloroformate, maleimide, alkene, silane, hydrazone, oxime and furan; or
   a bioactive group selected from the group consisting of avidin or streptavidin; antibody; sugars; and a protein or peptide sequence having a specific binding affinity for an affinity target; and
   L represents a spacer which is an ethylene glycol derivative of formula —[CH$_2$—CH$_2$—O]n$_2$-(CH$_2$)n$_3$-S— wherein n$_2$ and n$_3$ are each independently positive integers and n$_2$+n$_3$ is higher than 2 and wherein L is linked to Poly[(A)$_x$-co-(B)$_y$]$_n$ through the S atom of —[CH$_2$—CH$_2$—O]n$_2$-(CH$_2$)n$_3$-S— group.

9. The nanomaterial according to claim 1, wherein the at least one ligand is a copolymer of general formula (III):

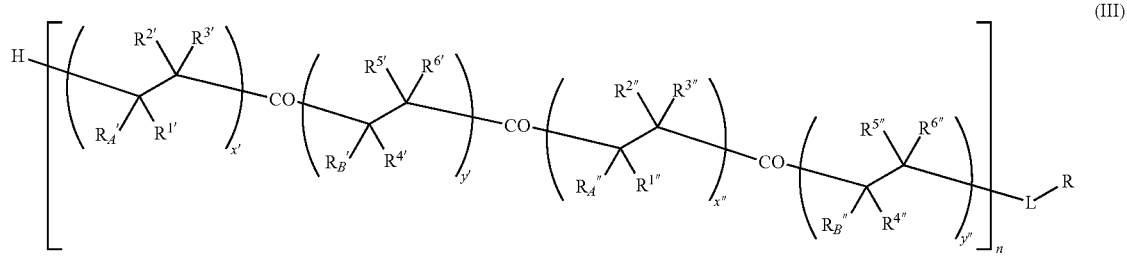

(III)

wherein
   co, L and R are as defined in claim 1,
   R$_A$' and R$_A$" represent respectively a group comprising a first moiety M$_A$' and a group comprising a first moiety M$_A$", said moieties M$_A$' and M$_A$" having affinity for the surface of a nanocrystal comprising a metal;
   R$_B$' and R$_B$" represent respectively a group comprising a second moiety M$_B$' and a group comprising a second moiety M$_B$", said moieties M$_B$' and M$_B$" being hydrophilic;
   R$^{1'}$, R$^{2'}$ R$^{3'}$, R$^{4'}$, R$^{5'}$, R$^{6'}$, R$^{1''}$, R$^{2''}$, R$^{3''}$, R$^{4''}$, R$^{5''}$ and R$^{6''}$ represent each independently H or a group selected from the group consisting of alkyl, alkenyl, aryl, hydroxyl, halogen, alkoxy, carboxylate, and amide;

n represents a positive integer;

x' and x" represent each independently a percentage of n, wherein at least one of x' and x" is different from 0% of n; wherein x' and x" are different from 100% of n;

y' and y" represent each independently a percentage of n, wherein at least one of y' and y" is different from 0% of n; wherein y' and y" are different from 100% of n; and wherein x'+x"+y'+y" is equal to 100% of n.

10. The nanomaterial according to claim 9, wherein x" and/or y" is equal to 0.

11. The nanomaterial according to claim 9, wherein $M_A'$ and $M_A''$ are each independently selected from an imidazole moiety and a carboxylic acid or carboxylate moiety, and $M_B'$ and $M_B''$ are each independently selected from a group with both an ammonium group and a sulfonate group, a sulfobetaine group, a PEG, a poly(ether)glycol moiety, a carboxybetaine moiety wherein the ammonium group may be included in a five-membered heterocycle comprising 1, 2 or 3 further nitrogen atoms, a sulfobetaine moiety wherein the ammonium group may be included in a five-membered heterocycle comprising 1, 2 or 3 further nitrogen atoms and a phosphobetaine wherein the ammonium group may be included in a five-membered heterocycle comprising 1, 2 or 3 further nitrogen atoms.

* * * * *